US011767299B2

(12) United States Patent
Stengel et al.

(10) Patent No.: US 11,767,299 B2
(45) Date of Patent: Sep. 26, 2023

(54) MATERIALS FOR ORGANIC ELECTROLUMINESCENT DEVICES

(71) Applicant: Merck Patent GmbH, Darmstadt (DE)

(72) Inventors: Ilona Stengel, Gorxheimertal (DE); Kathy Vinokurov, Dreieich (DE); Frank Voges, Bad Duerkheim (DE); Aurélie Ludemann, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 423 days.

(21) Appl. No.: 16/623,633

(22) PCT Filed: Jun. 20, 2018

(86) PCT No.: PCT/EP2018/066323
§ 371 (c)(1),
(2) Date: Dec. 17, 2019

(87) PCT Pub. No.: WO2018/234346
PCT Pub. Date: Dec. 27, 2018

(65) Prior Publication Data
US 2020/0190039 A1 Jun. 18, 2020

(30) Foreign Application Priority Data
Jun. 23, 2017 (EP) .................................... 17177694

(51) Int. Cl.
*C07D 237/26* (2006.01)
*C07C 49/597* (2006.01)
*C07C 49/653* (2006.01)
*H10K 85/60* (2023.01)
H10K 30/30 (2023.01)
H10K 50/15 (2023.01)

(52) U.S. Cl.
CPC .......... *C07D 237/26* (2013.01); *C07C 49/597* (2013.01); *C07C 49/653* (2013.01); *H10K 85/6572* (2023.02); H10K 30/353 (2023.02); H10K 50/15 (2023.02)

(58) Field of Classification Search
CPC .. C07D 237/26; C07D 495/04; C07D 251/12; C07D 487/14; C07C 49/597; C07C 49/653; C07C 255/35; C07C 255/37; C07C 255/40; C07C 255/00; H01L 51/0072; H01L 51/4273; H01L 51/5056; Y02E 10/549; C07F 5/027; C07F 9/65685
See application file for complete search history.

(56) References Cited

U.S. PATENT DOCUMENTS

| | | |
|---|---|---|
| 2,937,089 A | 5/1960 | Jones et al. |
| 4,539,507 A | 9/1985 | VanSlyke et al. |
| 9,917,272 B2 | 3/2018 | Voges et al. |
| 2003/0008174 A1 | 1/2003 | Suzuki et al. |
| 2010/0044686 A1 | 2/2010 | Morishita |
| 2011/0284827 A1* | 11/2011 | Morishita ........... H01L 51/0072 257/40 |
| 2015/0155513 A1 | 6/2015 | Pieh et al. |

FOREIGN PATENT DOCUMENTS

| | | |
|---|---|---|
| EP | 1284258 A2 | 2/2003 |
| EP | 1950817 A1 | 7/2008 |
| EP | 2045848 A1 | 4/2009 |
| EP | 2213662 A1 | 8/2010 |
| EP | 2371812 A1 | 10/2011 |
| EP | 2833429 A1 | 2/2015 |
| JP | 2002260863 A | 9/2002 |
| JP | 2003109764 A | 4/2003 |
| JP | 2005121887 A | 5/2005 |
| JP | 2015065248 A | 4/2015 |
| WO | WO-200149806 A1 | 7/2001 |
| WO | WO-201133023 A1 | 3/2011 |
| WO | WO-2012031735 A1 | 3/2012 |
| WO | WO-2014056565 A1 | 4/2014 |
| WO | WO-2014122933 A1 | 8/2014 |
| WO | WO-2015162912 A1 | 10/2015 |

OTHER PUBLICATIONS

Maxime Romain "ortho-, meta-, and para-Dihydroindenofluorene Derivatives as Host Materials for Phosphorescent OLEDs" Angew. Chem. Int. Ed. 2015, 54, 1176-1180 (Year: 2015).*
Maxime Romain "The structure-property relationship study of electron-deficient dihydroindeno[2,1-b]fluorene derivatives for n-type organic field effect transistors" J. Mater. Chem. C, 2015, 3, 5742 (Year: 2015).*
Tayebeh Hadizad "A General Synthetic Route to Indenofluorene Derivatives as New Organic Semiconductors" Organic Letters 2005 vol. 7, No. 5 (Year: 2005).*
International Search Report for PCT/EP2018/066323 dated Aug. 16, 2018.
Kojima, T., et al., "Synthesis of Triphosphatruxene via Sextuple Aromatic Nucleophilic Substitution and Simple Isolation of Stereoisomers", Chemical Letters, vol. 43, No. 5, (2014), pp. 676-677.
Nielsen, C., et al., "Electron-deficient truxenone derivatives and their use in organic photovoltaics", Journal of Materials Chemistry A, vol. 2, No. 31, (2014), pp. 12348-12354.
Romain, M., et al., "Donor/Acceptor Dihydroindeno[1,2-a]fluorene and Dihydroindeno[2,1-b]fluorene: Towards New Families of Organic Semiconductors", Chemistry—A European Journal, vol. 21, No. 26, (2015), pp. 9426-9439.
Romain, M., et al., "The structure-property relationship study of electron-deficient dihydroindeno[2,1-b]fluorene derivatives for n-type organic field effect transistors", Journal of Materials Chemistry C, vol. 3, No. 22, (2015), pp. 5742-5753.
Written Opinion of the International Searching Authority for PCT/EP2018/066323 dated Aug. 16, 2018.

* cited by examiner

Primary Examiner — Michael Y Sun
(74) Attorney, Agent, or Firm — Faegre Drinker Biddle & Reath LLP

(57) ABSTRACT

The present invention relates to compounds of the formula (1) which are suitable for use in electronic devices, in particular organic electroluminescent devices, and to electronic devices which comprise these compounds.

7 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2018/066323, filed Jun. 20, 2018, which claims benefit of European Application No. 17177694.1, filed Jun. 23, 2017, both of which are incorporated herein by reference in their entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The development of functional compounds for use in electronic devices is currently the subject of intensive research. The aim is, in particular, the development of compounds which can be used to improve properties of electronic devices in one or more relevant points, such as, for example, power efficiency and lifetime of the device as well as colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and the functional principle of OLEDs are known to the person skilled in the art and are described, for example, in U.S. Pat. No. 4,539,507.

It is known that layers having a hole-transporting function (hole-transporting layers), for example hole-injection layers, hole-transport layers and electron-blocker layers have a great influence on the performance data of electronic devices.

Indeed, the efficiency and lifetime of OLEDs are determined, inter alia, by the charge-carrier balance of electrons and holes in the device. This balance becomes established through the charge-carrier distribution and the associated field distribution in the device.

Efficient hole-injection is a major challenge in the fabrication of OLEDs. The absolute value of the work function of commonly used transparent anode material indium-tin oxide is typically below the absolute value of the highest occupied molecular orbital (HOMO) energies of common hole-transport materials.

Thus, there is a barrier for hole-injection into the hole-transport layer, which leads to an increase in the operating voltage of the OLED. This issue is typically approached by either doping the hole-transport layer with a p-dopant (for example like in WO 2014/056565), or by applying a hole-injection layer between the anode and the hole-transport layer (for example like in WO 2001/49806).

For good performance data, good mobilities of the charge carriers in the hole-transport layers and good hole-injection properties are particularly crucial. Furthermore, it is of crucial importance that the difference of the HOMOs of the materials of the various hole-transporting layers is not excessive.

The prior art discloses use of p-dopants (electron-acceptor compounds) in combination with hole-transport materials in hole-transporting layers (hole-injection layers, hole-transport layers and electron-blocker layers) of OLEDs. A p-dopant is understood here to mean a compound which, when added as a minor component to a main component, significantly increases the conductivity thereof.

Electron-acceptor compounds can also be used as the main component in a hole-transporting layer (for example, in the hole injection layer) in order to obtain layers having particularly good hole-injection properties.

P-dopants and, in a more general way, organic electron-acceptor compounds are known from the prior art, for example 7,7,8,8-tetracyano-2,3,5,6-tetrafluoroquinodimethane (F4TCNQ). The prior art further discloses, as electron acceptor compounds, metal complexes of transition metal cations and main group metal cations, for example in WO 2011/33023 and indenofluorenedione derivatives, for example in EP 2045848.

However, there is a demand for alternative materials that can be used as electron-acceptor materials in OLEDs. Moreover, further improvements with regard to this type of compounds are still desirable either to improve the OLEDs performances with respect to the lifetime and the efficiency and/or to improve the handling of these compounds. There is a need for materials that are efficient as electron-acceptor materials due to appropriate electronic properties, for example by having a high electron affinity. At the same time, these materials should also exhibit appropriate physico-chemical properties, for example in terms of solubility and stability, in order to be optimally synthesized, purified and processed during the fabrication of the OLEDs. Furthermore, the materials employed as electron-acceptor materials (for example as p-dopants or as main components in a hole-injection layer) in an OLED should absorb as little light as possible in the visible region (VIS region). The absence of significant absorption bands in the VIS region is highly desirable since absorptions in the VIS region affect the emission characteristics of the OLEDs and their efficiency.

The present invention is thus based on the technical object of providing an electron-acceptor material as a p-dopant or as a main component in a hole-transporting layer selected from hole-injection layers, hole-transport layers and electron-blocker layers, for use in electronic devices.

In investigations on novel compounds for use in electronic devices, it has now been found, unexpectedly, that compounds of formula (1) as defined below are eminently suitable for use in electronic devices and at the same time, these compounds have good solubility, which facilitates their purification and their handling and they exhibit a lower absorption in the visible region (VIS region). In particular, these compounds enable to efficiently decrease the operating voltage of OLEDs, in which they are employed and they show good processability during the evaporation process for vapour processed OLEDs.

The present application thus relates to the compounds of formula (1),

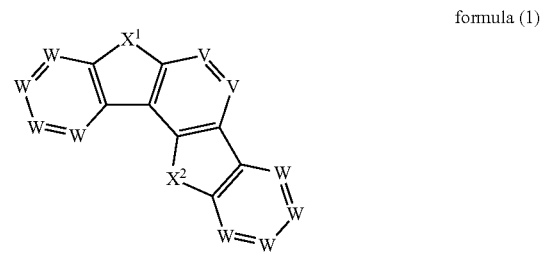

formula (1)

where the following applies to the symbols and indices used:
V is on each occurrence, identically or differently, $CR^1$ or N; or the two adjacent groups V stand for a group of formula (Z-1),

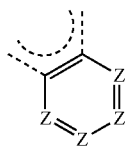

Formula (Z-1)

where the dashed bonds in formula (Z-1) indicate the bonding to the structure of formula (1); and Z is on each occurrence, identically or differently, $CR^2$ or N;

W is $CR^2$ or N; or two adjacent groups W stand for a group of formula (Z-1);

$X^1$, $X^2$ are on each occurrence, identically or differently, selected from groups of formulae (X-1) to (X-9), with the proviso that $X^1$ and $X^2$ are not both a group of formula (X-1) in a compound of formula (1);

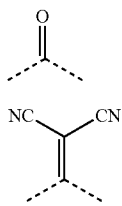
(X-1)
(X-2)
(X-3)

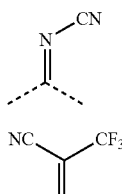
(X-4)
(X-5)

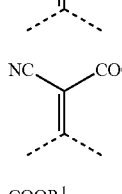
(X-6)

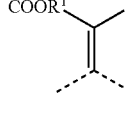
(X-7)

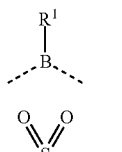
(X-8)

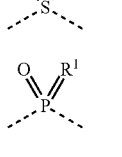
(X-9)

where the dashed bonds in formulae (X-1) to (X-9) indicate the bonds to the 5-membered ring comprising $X^1$ or $X^2$;

$R^1$, $R^2$ stand on each occurrence, identically or differently, for H, D, F, Cl, Br, I, CHO, CN, $N(R^3)_2$, $N(Ar)_2$, C(=O)Ar, P(=O)$(Ar)_2$, S(=O)Ar, S(=O)$_2$Ar, $NO_2$, $Si(R^3)_3$, $B(OR^3)_2$, $OSO_2R^3$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^3$, where in each case one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, P(=O)$(R^3)$, SO, $SO_2$, O, S or $CONR^3$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^3$, or an aryloxy groups having 5 to 60 aromatic ring atoms, which may be substituted by one or more radicals $R^3$, where two adjacent substituents $R^1$ and/or two adjacent substituents $R^2$ may form a mono- or polycyclic, aliphatic ring system or aromatic ring system, which may be substituted by one or more radicals $R^3$;

$R^3$ stands on each occurrence, identically or differently, for H, D, F, Cl, Br, I, CHO, CN, $N(Ar)_2$, C(=O)Ar, P(=O)$(Ar)_2$, S(=O)Ar, S(=O)$_2$Ar, $NO_2$, $Si(R^4)_3$, $B(OR^4)_2$, $OSO_2R^4$, a straight-chain alkyl, alkoxy or thioalkyl groups having 1 to 40 C atoms or branched or cyclic alkyl, alkoxy or thioalkyl groups having 3 to 40 C atoms, each of which may be substituted by one or more radicals $R^4$, where in each case one or more non-adjacent $CH_2$ groups may be replaced by $R^4C=CR^4$, C≡C, $Si(R^4)_2$, $Ge(R^4)_2$, $Sn(R^4)_2$, C=O, C=S, C=Se, P(=O)$(R^4)$, SO, $SO_2$, O, S or $CONR^4$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^4$, or an aryloxy group having 5 to 60 aromatic ring atoms, which may be substituted by one or more radicals $R^4$, where two adjacent substituents $R^3$ may form a mono- or polycyclic, aliphatic ring system or aromatic ring system, which may be substituted by one or more radicals $R^4$;

$R^4$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 C atoms;

Ar is on each occurrence, identically or differently, an aromatic or heteroaromatic ring system having 5 to 60 aromatic ring atoms, which may in each case also be substituted by one or more radicals $R^4$.

Furthermore, the following definitions of chemical groups apply for the purposes of the present application:

An aryl group in the sense of this invention contains 6 to 60 aromatic ring atoms, preferably 6 to 40 aromatic ring atoms, more preferably 6 to 20 aromatic ring atoms; a heteroaryl group in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group ("—OAr") in accordance with the definition of the present invention is taken to mean an aryl group, as defined above, which is bonded via an oxygen atom to a structure.

An analogous definition applies to heteroaryloxy groups.

An aromatic ring system in the sense of this invention contains 6 to 60 C atoms in the ring system, preferably 6 to 40 C atoms, more preferably 6 to 20 C atoms. A heteroaromatic ring system in the sense of this invention contains 5 to 60 aromatic ring atoms, preferably 5 to 40 aromatic ring atoms, more preferably 5 to 20 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenyl-ene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-tri-fluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethyl-thio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

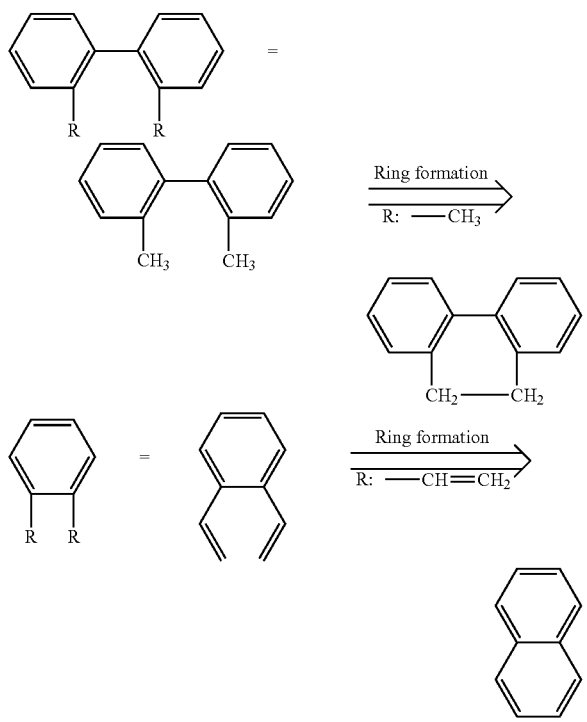

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

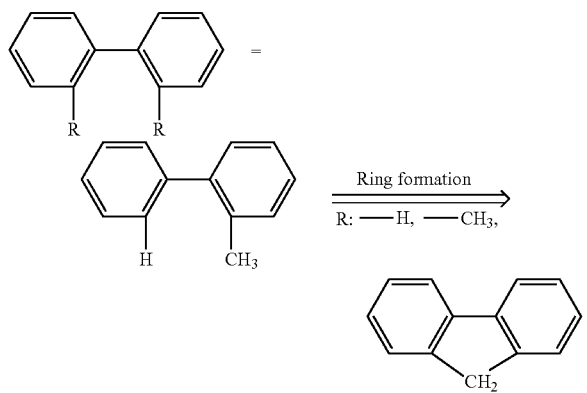

Furthermore, for the purposes of the present application, a hole-transport material can be a hole-transport material (HTM) and/or a hole-injection material (HIM). Hole-injection materials simplify or facilitate the transfer of holes, i.e. positive charges, from the anode into an organic layer. Hole-transport materials are capable of transporting holes, i.e. positive charges, which are generally injected from the anode or an adjacent layer, for example a hole-injection layer.

These materials are frequently described via the properties of the frontier orbitals, which are described in greater detail below. Molecular orbitals, in particular also the highest occupied molecular orbital (HOMO) and the lowest unoccupied molecular orbital (LUMO), their energy levels and the energy of the lowest triplet state $T_1$ or of the lowest excited singlet state Si of the materials are determined via quantum-chemical calculations. In order to calculate organic substances without metals, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SCF/DFT/Default Spin/B3PW91" method with the "6-31G(d)" base set (charge 0, spin singlet) is used here. For metal-containing compounds, the geometry is optimised via the "Ground State/Hartree-Fock/Default Spin/LanL2 MB/Charge 0/Spin Singlet" method. The energy calculation is carried out analogously to the above-described method for the organic substances, with the difference that the "LanL2DZ" base set is used for the metal atom and the "6-31G(d)" base set is used for the ligands. The energy calculation gives the HOMO energy level HEh or LUMO energy level LEh in hartree units. The HOMO and LUMO energy levels in electron volts calibrated with reference to cyclic voltammetry measurements are determined therefrom as follows:

HOMO(eV)=((*HEh*\*27.212)−0.9899)/1.1206

LUMO(eV)=((*LEh*\*27.212)−2.0041)/1.385

For the purposes of this application, these values are to be regarded as HOMO and LUMO energy levels respectively of the materials.

The lowest triplet state $T_1$ is defined as the energy of the triplet state having the lowest energy which arises from the quantum-chemical calculation described.

The lowest excited singlet state Si is defined as the energy of the excited singlet state having the lowest energy which arises from the quantum-chemical calculation described.

The method described herein is independent of the software package used and always gives the same results. Examples of frequently used programs for this purpose are "Gaussian09 W" (Gaussian Inc.) and Q-Chem 4.1 (Q-Chem, Inc.).

In general, a hole-injection material has an HOMO level which is in the region of or above the level of the anode, i.e. in general is at least −5.3 eV. A hole-transport material generally has a high HOMO level of preferably at least −5.4 eV. Depending on the structure of an electronic device, it may also be possible to employ a hole-transport material as hole-injection material.

In accordance with a preferred embodiment, the compounds of formula (1) are selected from compounds of the following formulae (2) to (9),

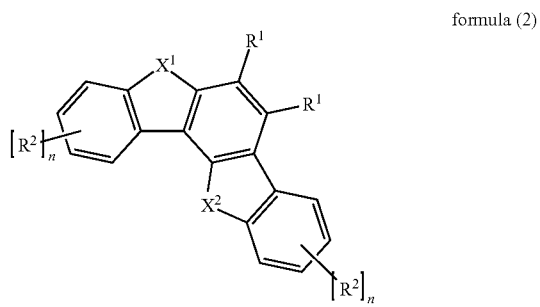

formula (2)

formula (3)
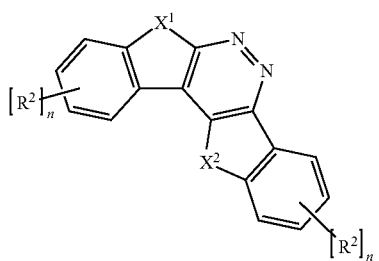

formula (4)
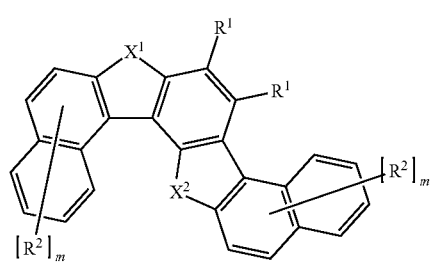

formula (5)
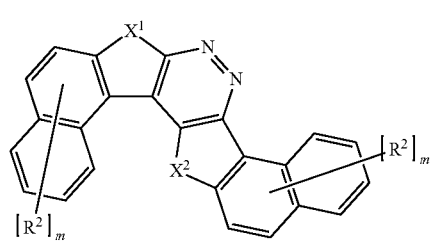

formula (6)
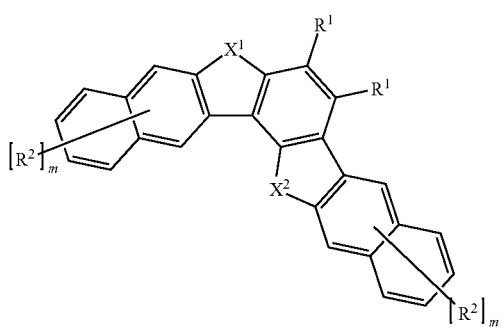

formula (7)
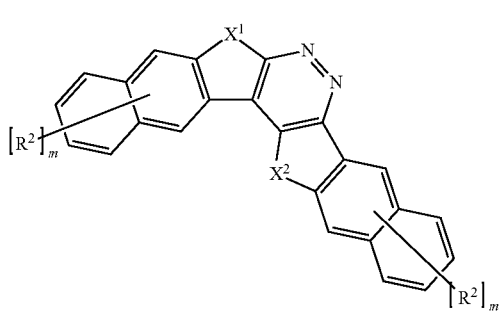

formula (8)
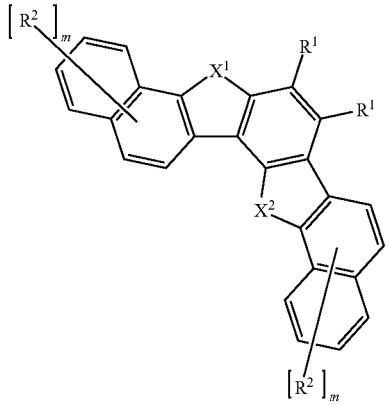

formula (9)
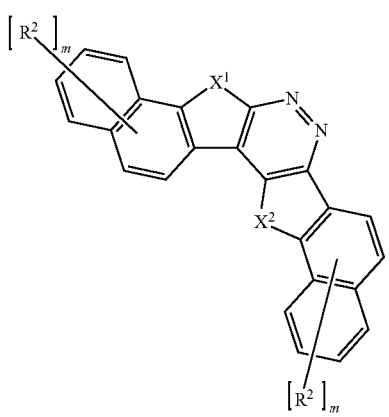

where the symbols $X^1$, $X^2$, $R^1$ and $R^2$ have the same meaning as above, and where
the index n is an integer from 0 to 4; and
the index m is an integer from 0 to 6.

Preferably, n is equal to 1 in formulae (2) and (3) and m is equal to 1 or 2 in formulae (4) to (9).

In accordance with a very preferred embodiment, the compounds of formula (1) are selected from the compounds of the following formulae (10) to (19), formula (10)
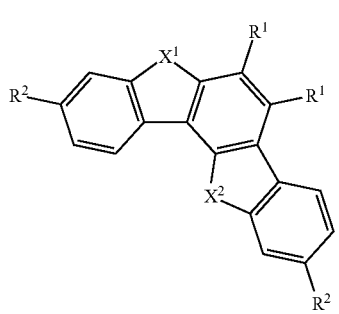

formula (11)
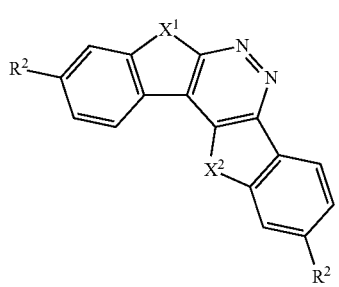

-continued formula (12)
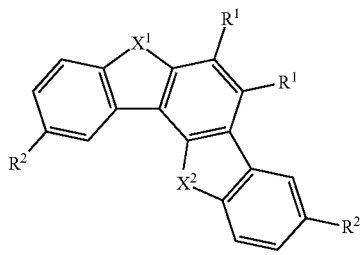

formula (13)
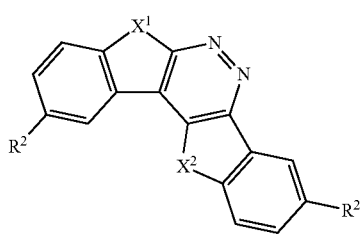

formula (14)
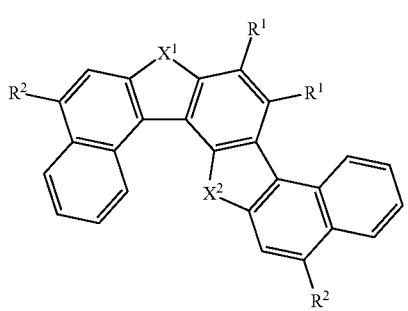

formula (15)
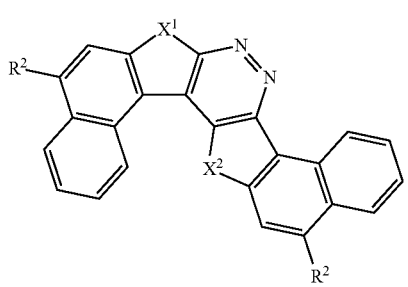

formula (16)
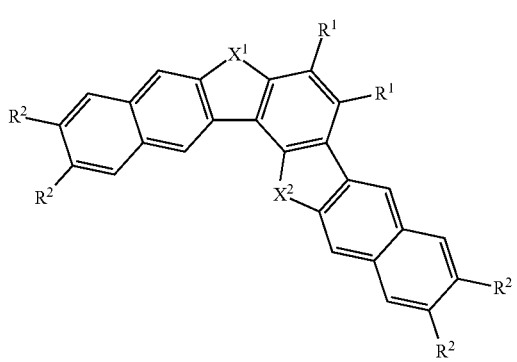

-continued formula (17)
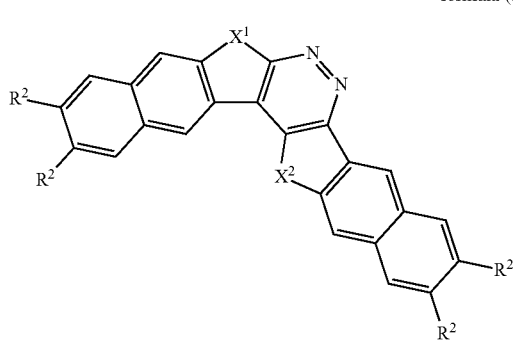

formula (18)
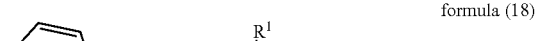

formula (19)
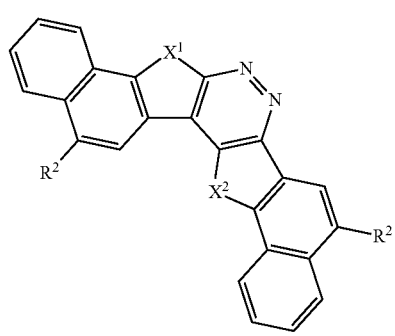

where the symbols $X^1$, $X^2$, $R^1$ and $R^2$ have the same meaning as above.

In accordance with a preferred embodiment, $X^1$ corresponds to one of the groups of formulae (X-2) to (X-9), preferably one of the groups of formulae (X-2) to (X-6), very preferably one of the groups of formulae (X-2) to (X-3), and $X^2$ corresponds to a group of formula (X-1) as defined above.

Very preferably $X^1$ corresponds to (X-2) and $X^2$ corresponds to (X-1).

In accordance with another preferred embodiment, $X^1$ and $X^2$ are, on each occurrence, identically or differently, selected from the groups of formulae (X-2) to (X-9), preferably (X-2) to (X-6), very preferably (X-2) to (X-3). Particularly preferably, $X^1$ and $X^2$ both correspond to a group of formula (X-2).

In accordance with a very preferred embodiment, the compounds of formula (1) are selected from the compounds of formula (1A) or (1B):

formula (1A)
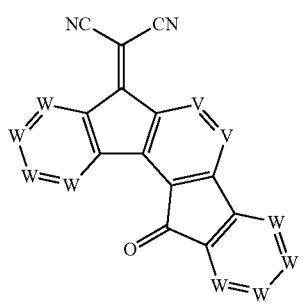
formula (1B)
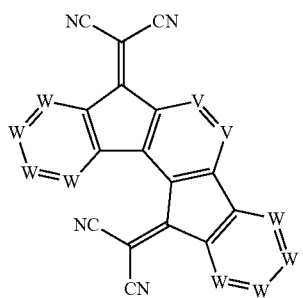
In accordance with a preferred embodiment, the compounds of formulae (1A) and (1B) are selected from compounds of the following formulae (2A) to (9B),
formula (2A)
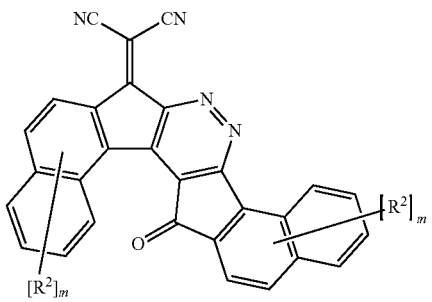
formula (3A)
formula (4A)
formula (5A)
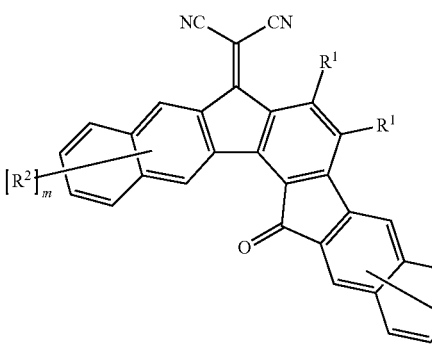
formula (6A)
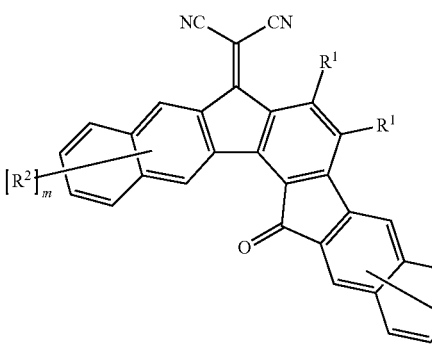
formula (7A)
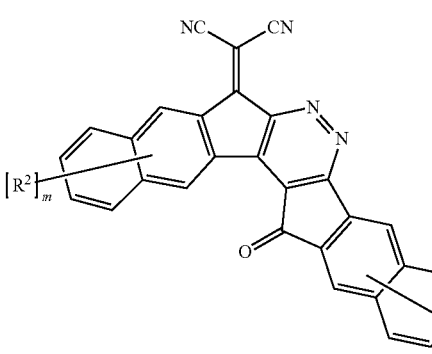
formula (8A)
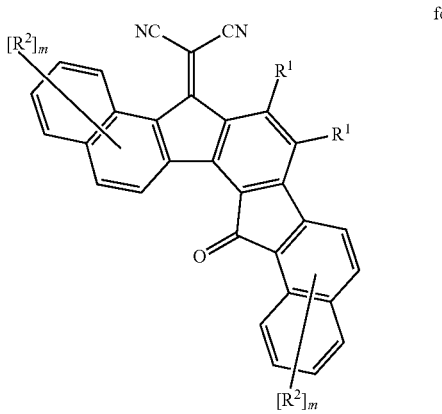

formula (9A)
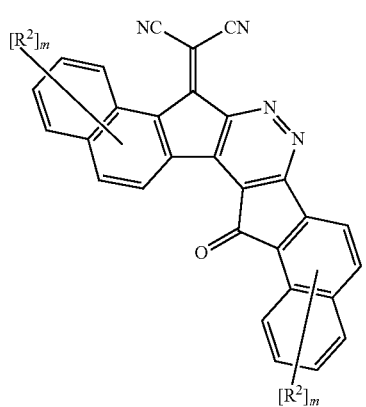
formula (2B)
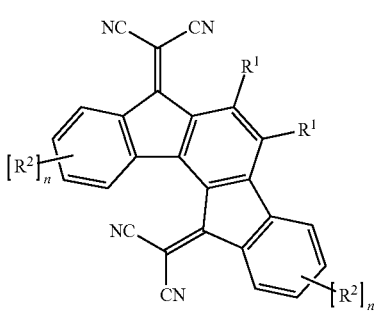
formula (3B)
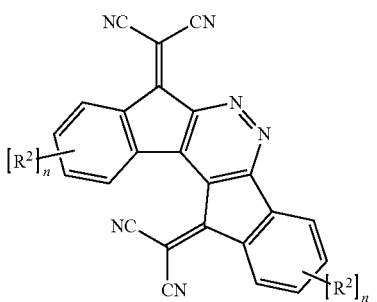
formula (4B)
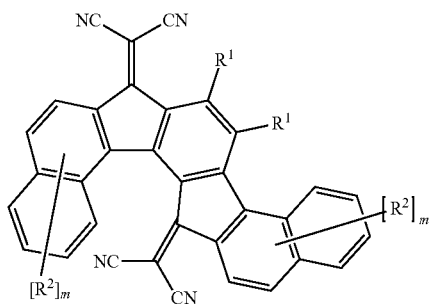
formula (5B)
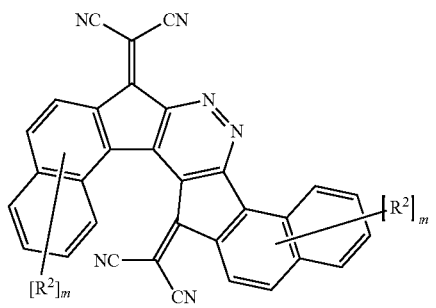
formula (6B)
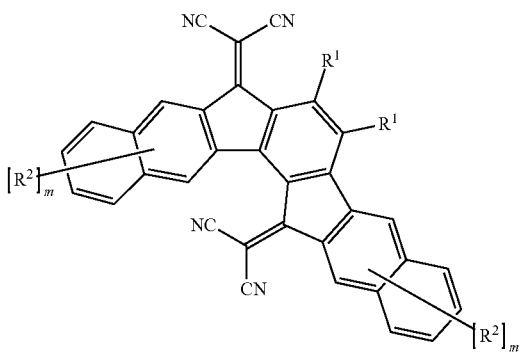
formula (7B)
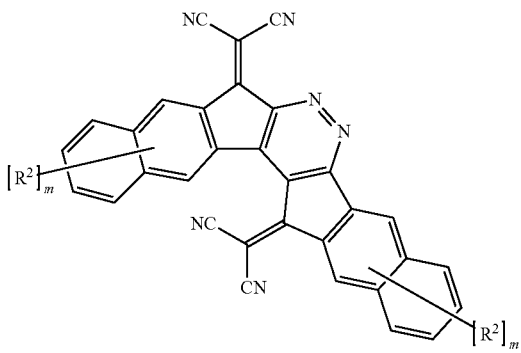
formula (8B)
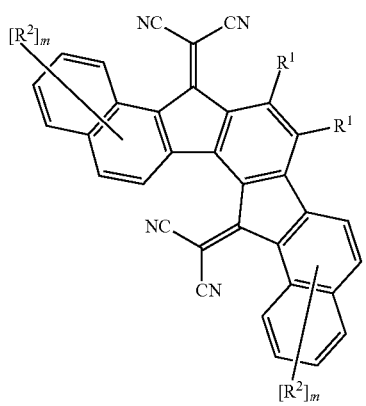

-continued
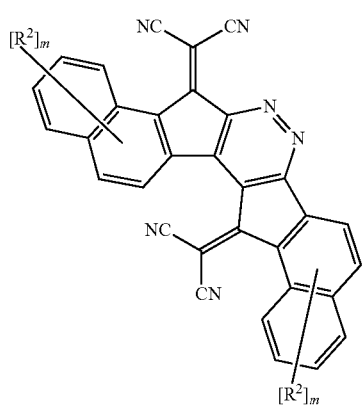
formula (9B)
where the symbols $X^1$, $X^2$, $R^1$, $R^2$ and the indices n and m have the same meaning as above.
In accordance with a very preferred embodiment, the compounds of formula (10) to (19) are selected from the compounds of the following formulae (10A) to (19B),
formula (10A)
formula (11A)
formula (12A)
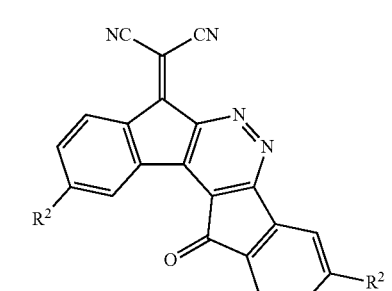
formula (13A)
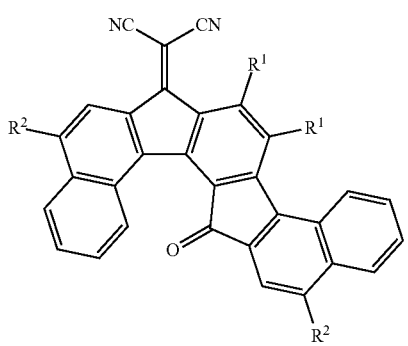
formula (14A)
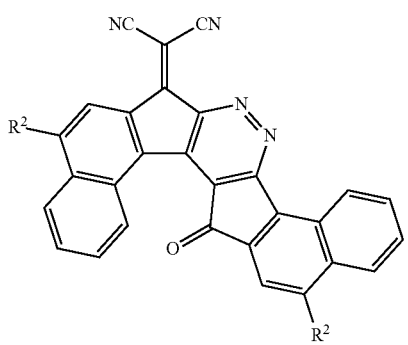
formula (15A)
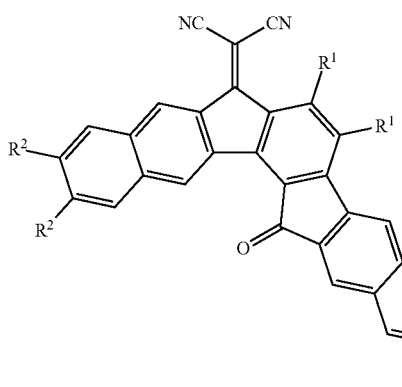
formula (16A)

-continued
formula (17A)
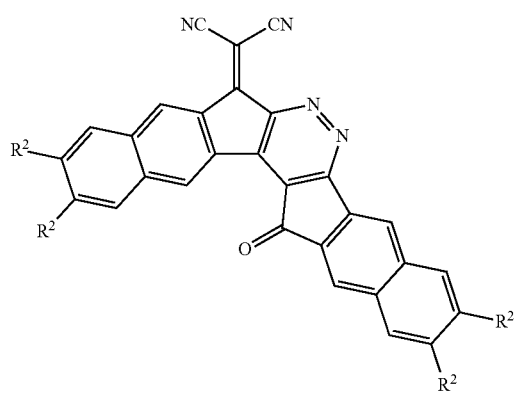
formula (18A)
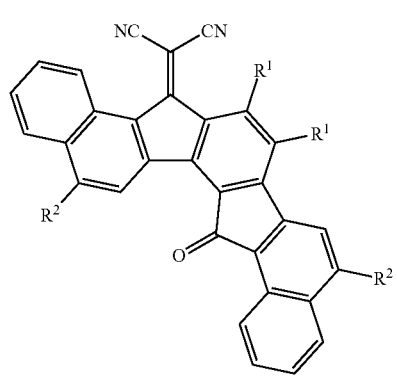
formula (19A)
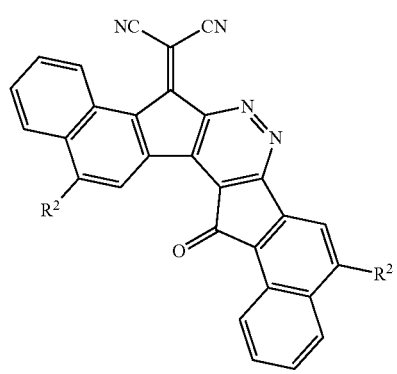
formula (10B)
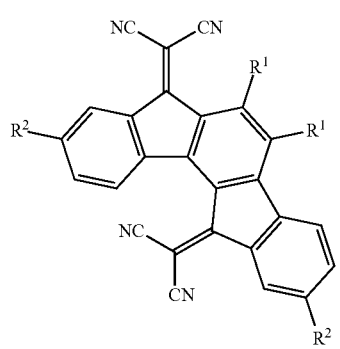
formula (11B)
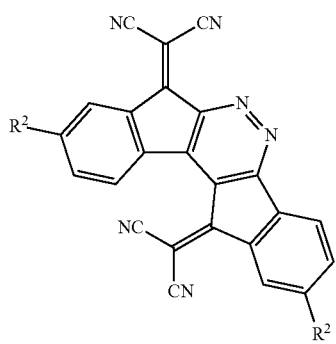
formula (12B)
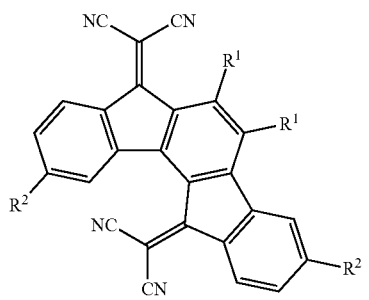
formula (13B)
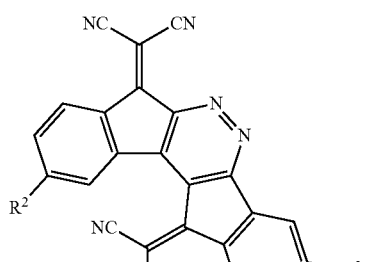
formula (14B)
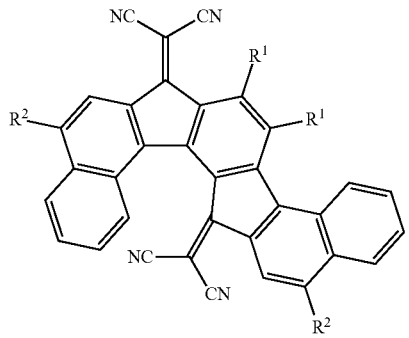
formula (15B)
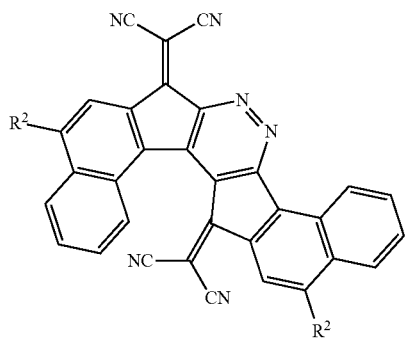

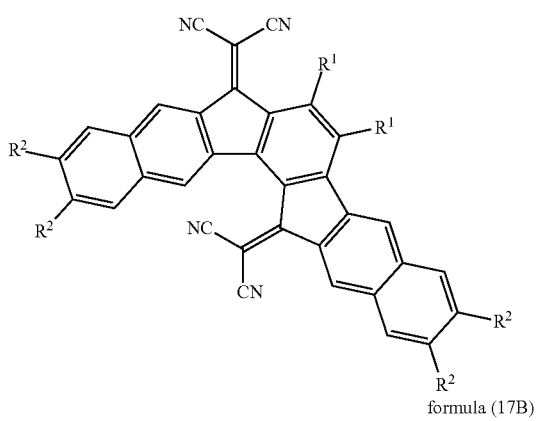

formula (16B)

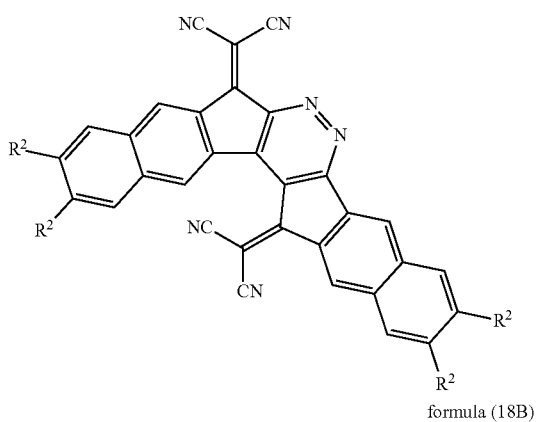

formula (17B)

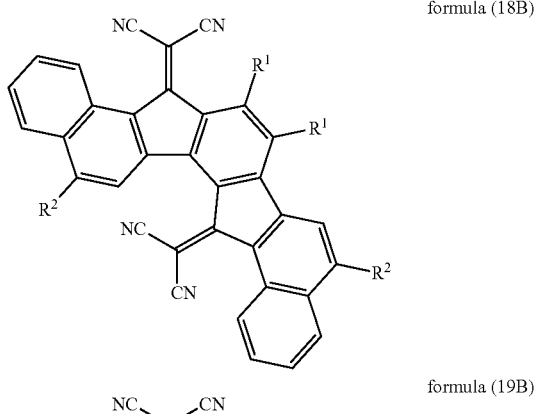

formula (18B)

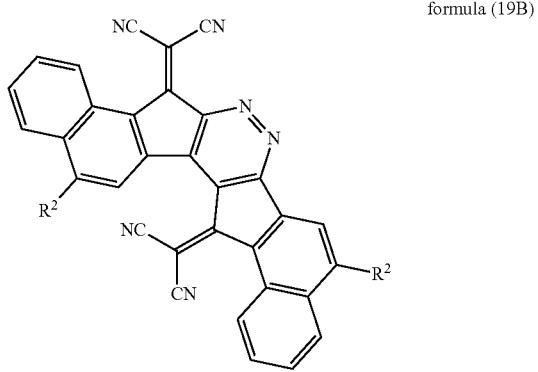

formula (19B)

where the symbols $R^1$ and $R^2$ have the same meaning as above.

In accordance with a preferred embodiment, the compounds of formulae (1), (1A) and (1B) comprise at least one group $R^2$, which is selected on each occurrence, identically or differently, from the group consisting of F, CN, a straight-chain alkyl, alkoxy or thioalkyl groups having 1 to 20 C atoms or a branched or a cyclic alkyl, alkoxy or thioalkyl groups having 3 to 20 C atoms, each of which may be substituted by one or more radicals $R^3$, where in each case one or more non-adjacent $CH_2$ groups may be replaced by $R^3C=CR^3$, C≡C, C=O, P(=O)($R^3$), SO, $SO_2$, O, S or $CONR^3$ and where one or more H atoms may be replaced by D or F, an aromatic or heteroaromatic ring systems having 5 to 30 aromatic ring atoms, which may in each case be substituted by one or more radicals $R^3$, or an aryloxy groups having 5 to 30 aromatic ring atoms, which may be substituted by one or more radicals $R^3$.

In accordance with a preferred embodiment, n is on each occurrence equal to 1 in formulae (2) and (3), (2A) and (3A), and (3A) and (3B) and m is on each occurrence equal to 1 or 2 in formulae (4) to (9), (4A) to (9A), and (4B) to (9B) and $R^2$ is selected on each occurrence, identically or differently, from the group consisting of F, CN, a straight-chain alkyl, alkoxy or thioalkyl groups having 1 to 20 C atoms or a branched or a cyclic alkyl, alkoxy or thioalkyl groups having 3 to 20 C atoms, each of which may be substituted by one or more radicals $R^3$, where in each case one or more non-adjacent $CH_2$ groups may be replaced by $R^3C=CR^3$, C≡C, C=O, P(=O)($R^3$), SO, $SO_2$, O, S or $CONR^3$ and where one or more H atoms may be replaced by D or F, an aromatic or heteroaromatic ring systems having 5 to 30 aromatic ring atoms, which may in each case be substituted by one or more radicals $R^3$, or an aryloxy groups having 5 to 30 aromatic ring atoms, which may be substituted by one or more radicals $R^3$.

In accordance with a preferred embodiment, in formulae (10) to (19) and (10A) to (19B), $R^2$ is selected on each occurrence, identically or differently, preferably identically, from the group consisting of F, CN, a straight-chain alkyl, alkoxy or thioalkyl groups having 1 to 20 C atoms or a branched or a cyclic alkyl, alkoxy or thioalkyl groups having 3 to 20 C atoms, each of which may be substituted by one or more radicals $R^3$, where in each case one or more non-adjacent $CH_2$ groups may be replaced by $R^3C=CR^3$, C≡C, C=O, P(=O)($R^3$), SO, $SO_2$, O, S or $CONR^3$ and where one or more H atoms may be replaced by D or F, an aromatic or heteroaromatic ring systems having 5 to 30 aromatic ring atoms, which may in each case be substituted by one or more radicals $R^3$, or an aryloxy groups having 5 to 30 aromatic ring atoms, which may be substituted by one or more radicals $R^3$.

It is preferable that $R^1$ stands on each occurrence, identically or differently, for H, D, F, CN, a straight-chain alkyl, alkoxy or thioalkyl groups having 1 to 20, preferably 1 to 10 C atoms or branched or a cyclic alkyl, alkoxy or thioalkyl groups having 3 to 20, preferably 3 to 10 C atoms, each of which may be substituted by one or more radicals $R^3$, where in each case one or more non-adjacent $CH_2$ groups may be replaced by $R^3C=CR^3$, C≡C, C=O, SO, $SO_2$, O or S and where one or more H atoms may be replaced by D or F, an aromatic or heteroaromatic ring systems having 5 to 40, preferably 5 to 30, very preferably 6 to 18 aromatic ring atoms, which may in each case be substituted by one or more radicals $R^3$, or an aryloxy groups having 5 to 40, preferably 5 to 30, very preferably 6 to 18 aromatic ring atoms, which may be substituted by one or more radicals $R^3$, where two adjacent substituents $R^1$ may form a mono- or polycyclic, aliphatic ring system or aromatic ring system, which may be substituted by one or more radicals $R^3$.

It is preferable that $R^3$ stands on each occurrence, identically or differently, for H, D, F, CN, a straight-chain alkyl, alkoxy or thioalkyl groups having 1 to 20, preferably 1 to 10 C atoms or branched or a cyclic alkyl, alkoxy or thioalkyl groups having 3 to 20, preferably 3 to 10 C atoms, each of which may be substituted by one or more radicals $R^4$, where in each case one or more non-adjacent $CH_2$ groups may be replaced by $R^3C=CR^3$, C≡C, C=O, SO, $SO_2$, O or S and where one or more H atoms may be replaced by D or F, an aromatic or heteroaromatic ring systems having 5 to 40, preferably 5 to 30, very preferably 6 to 18 aromatic ring atoms, which may in each case be substituted by one or more radicals $R^4$, or an aryloxy groups having 5 to 40, preferably 5 to 30, very preferably 6 to 18 aromatic ring atoms, which may be substituted by one or more radicals $R^4$.

It is preferable that $R^4$ stands on each occurrence, identically or differently, for H, D, F, Cl, Br, I, CN, a straight-chain alkyl, alkoxy or thioalkyl groups having 1 to 20, preferably 1 to 10 C atoms or branched or cyclic alkyl, alkoxy or thioalkyl groups having 3 to 20, preferably 3 to 10 C atoms, or an aromatic or heteroaromatic ring system having 5 to 18, preferably 6 to 12 C atoms.

The following compounds are examples of compounds of the formula (1):

1
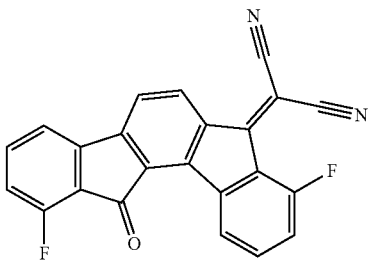

2
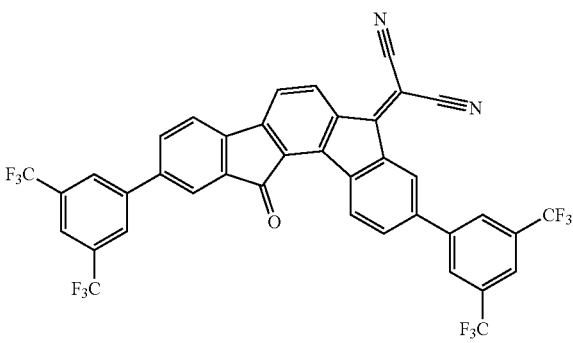

3
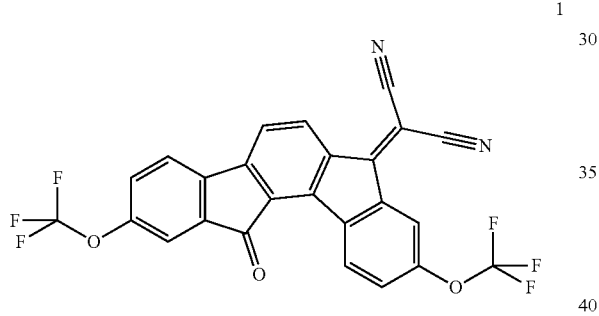

-continued

4
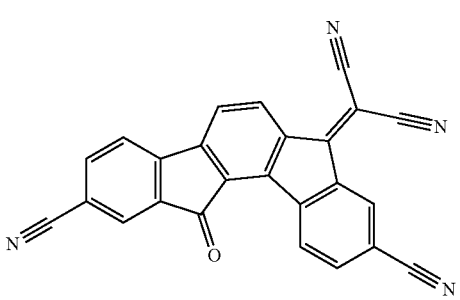

5
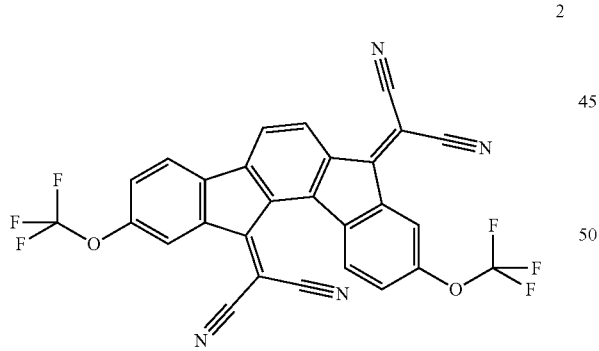

6
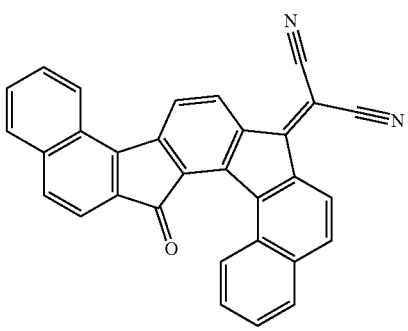

7
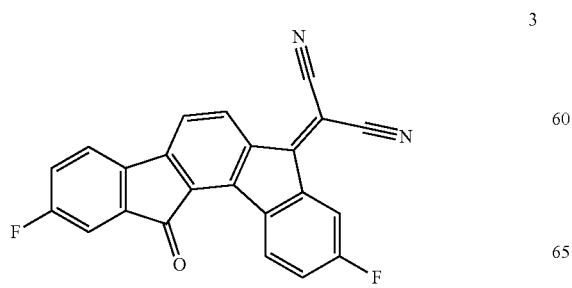

8
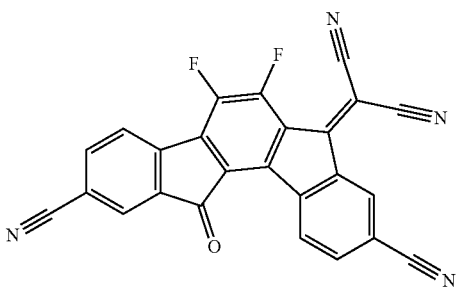

-continued
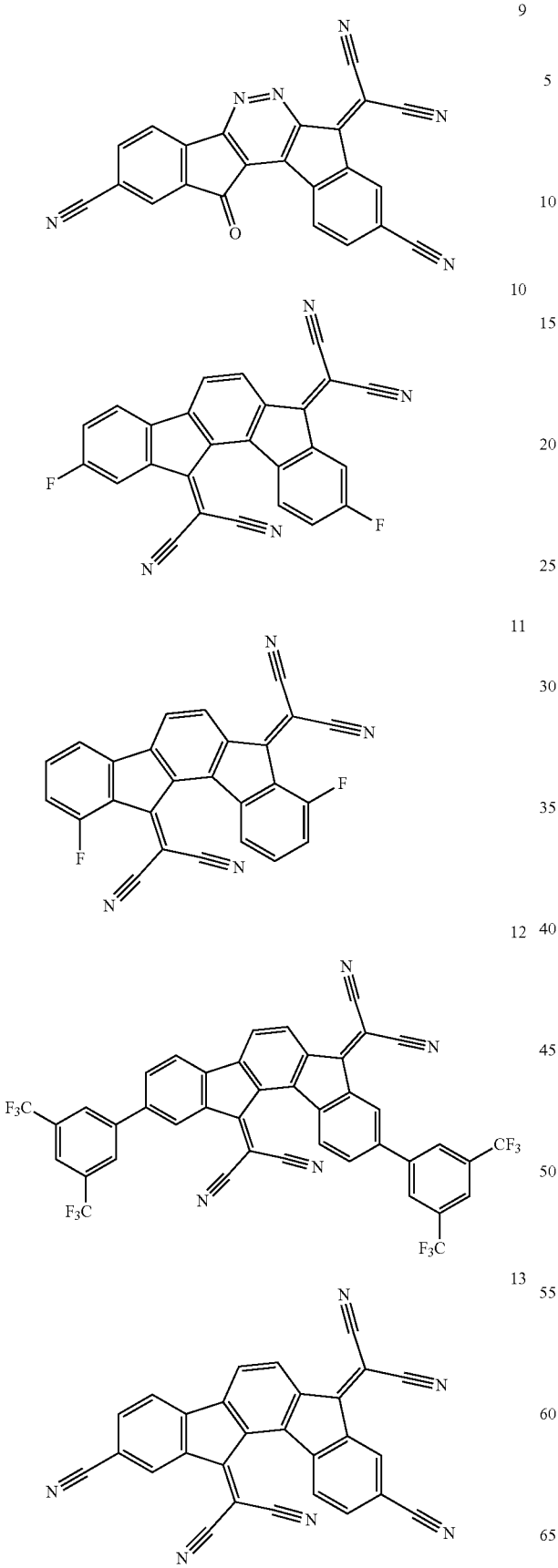
-continued
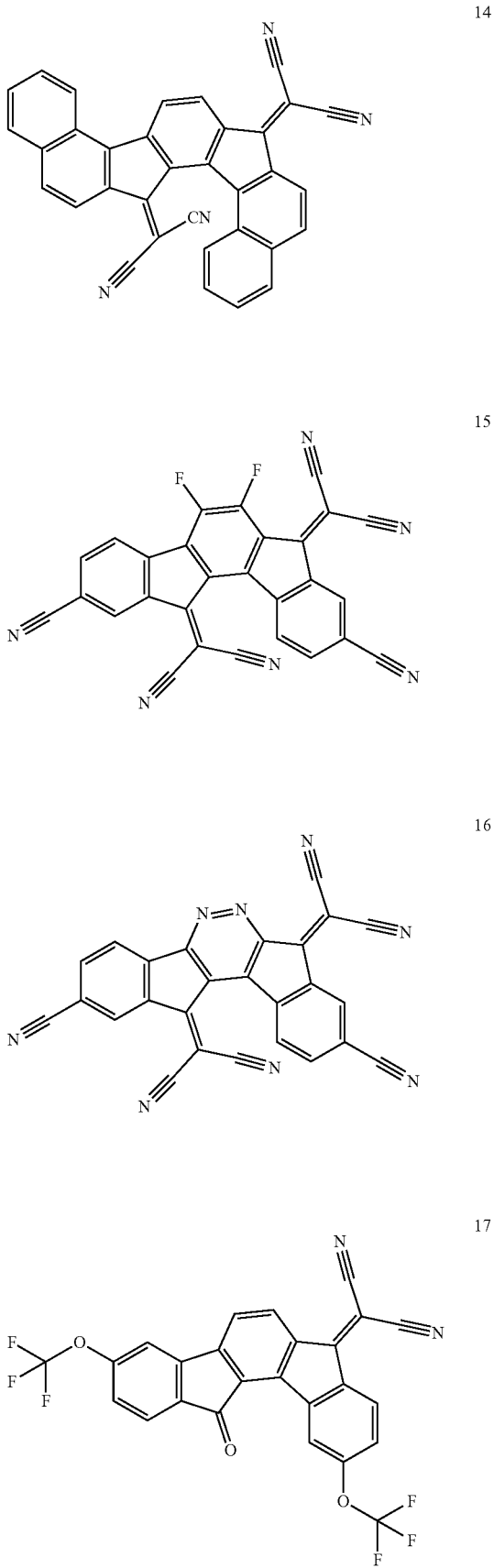

18
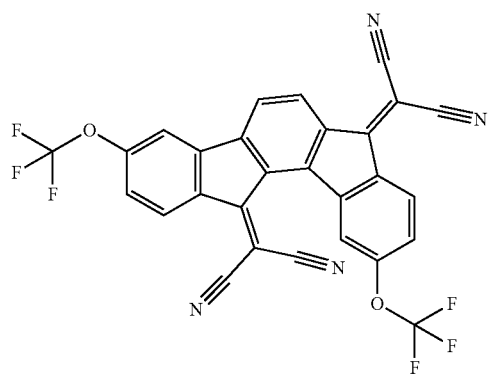
22
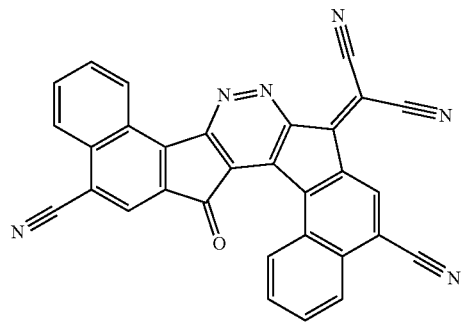
19
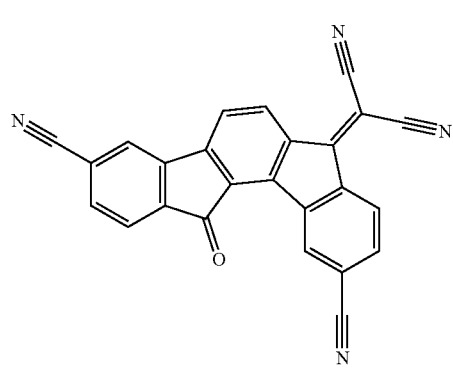
23
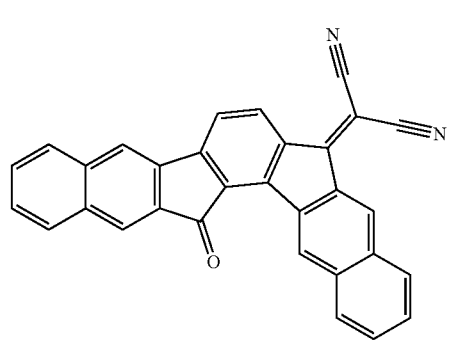
20
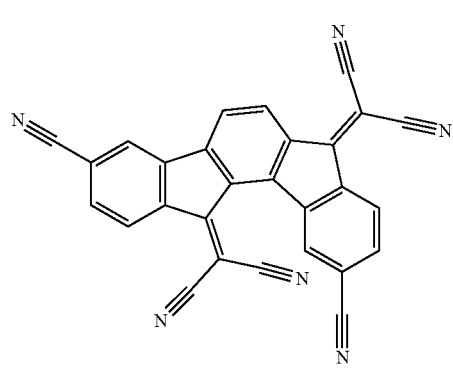
24
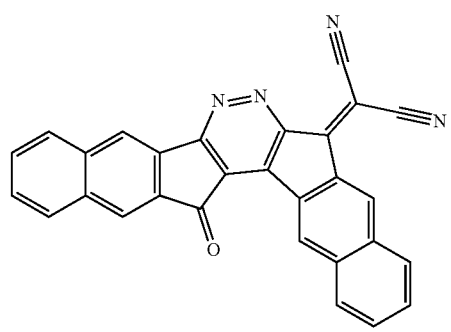
21
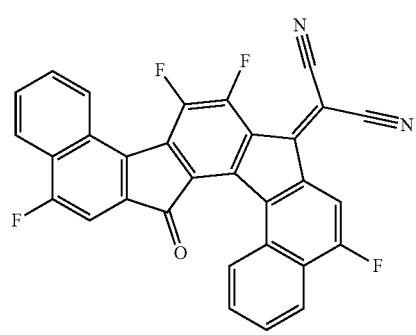
25
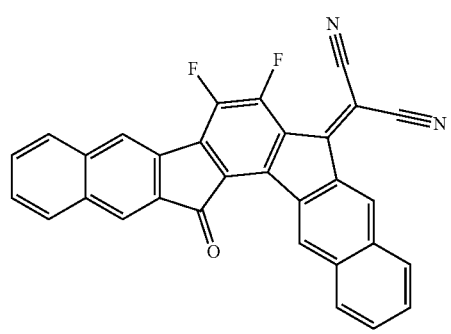

-continued
26
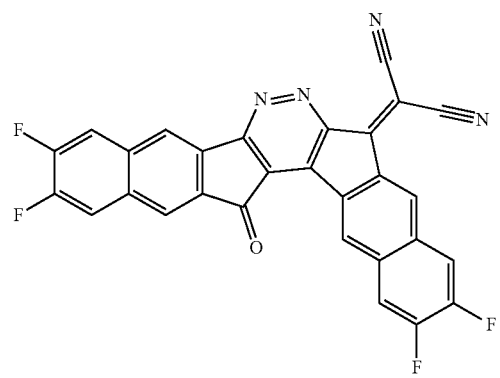
27
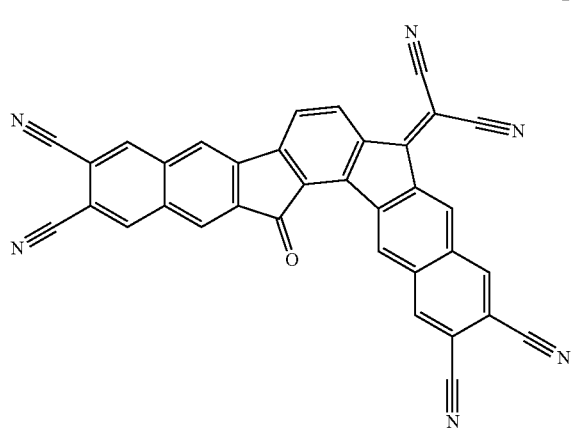
28
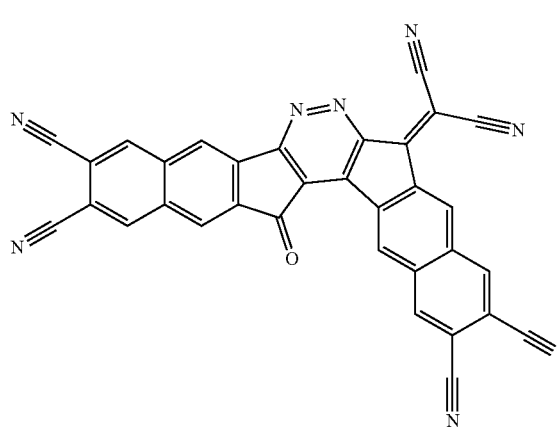
29
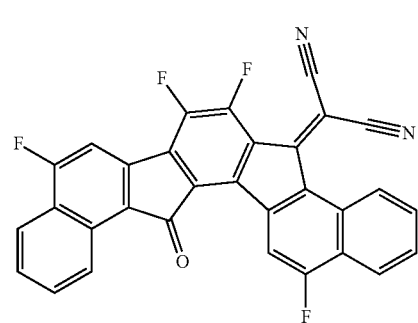
-continued
30
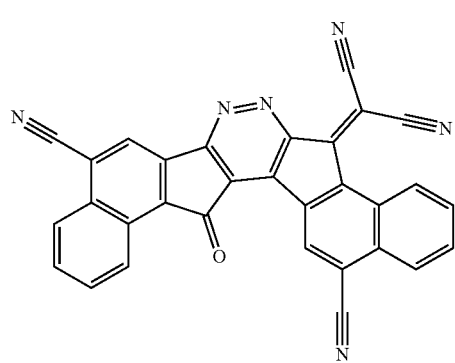
31
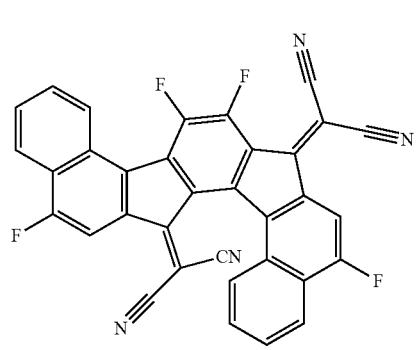
32
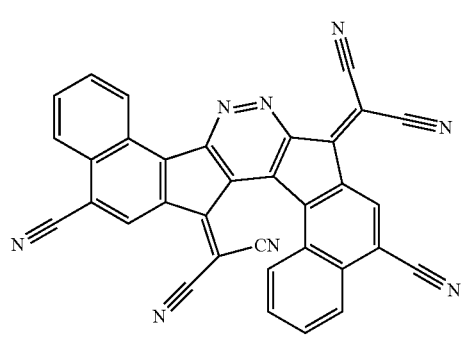
33
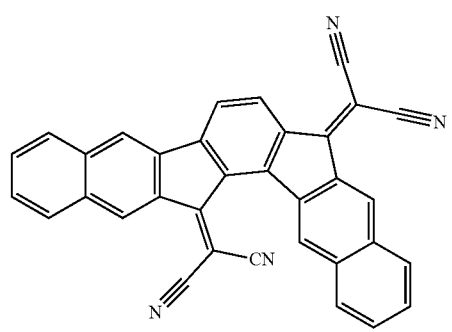

34
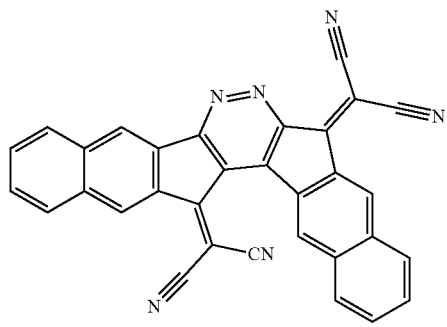
35
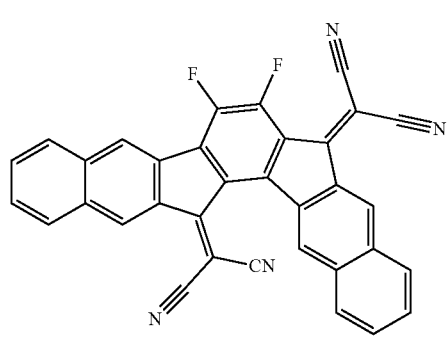
36
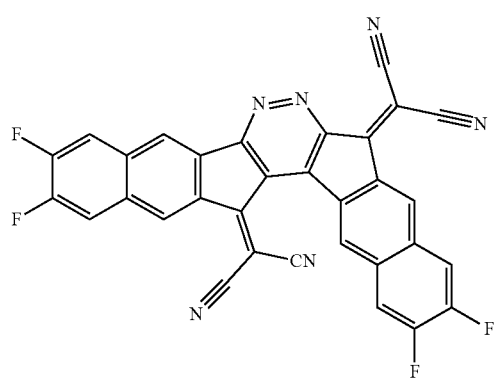
37
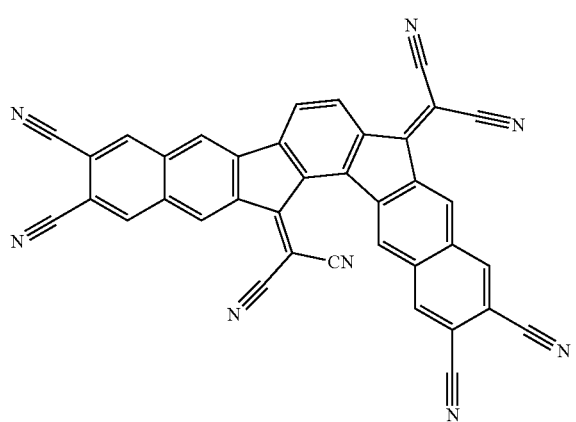
38
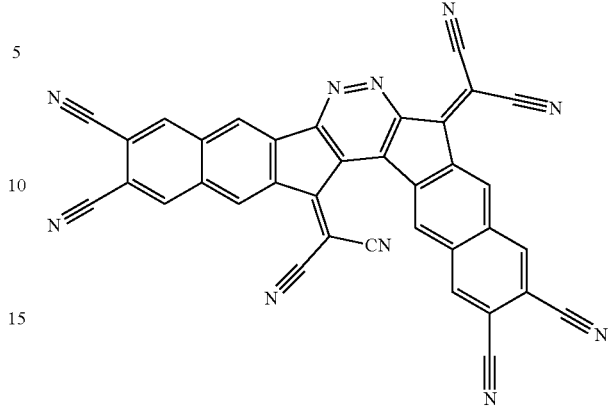
39
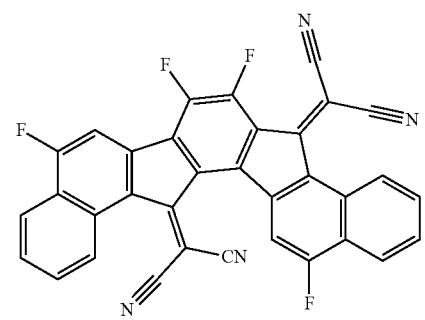
40
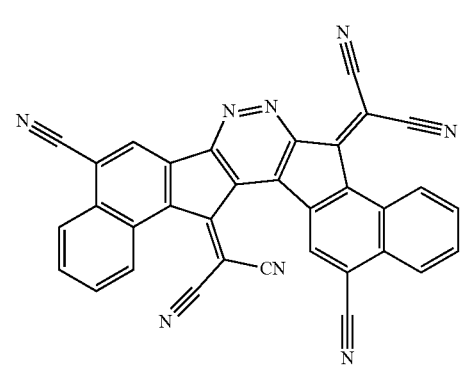
41
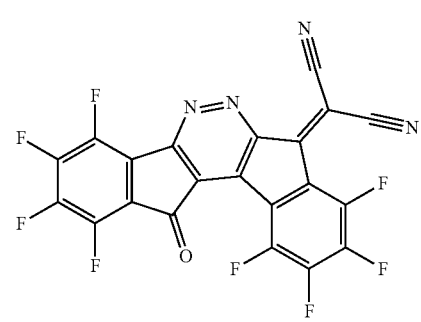

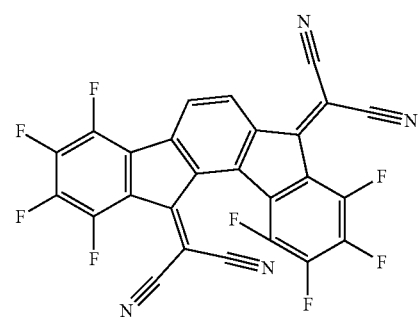
42
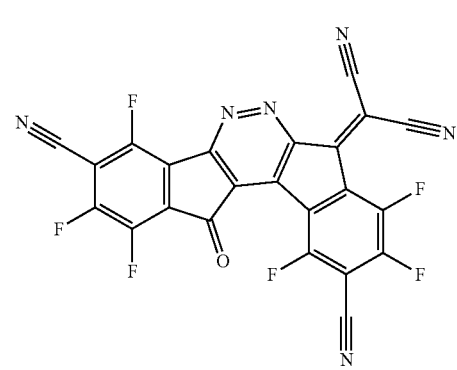
43
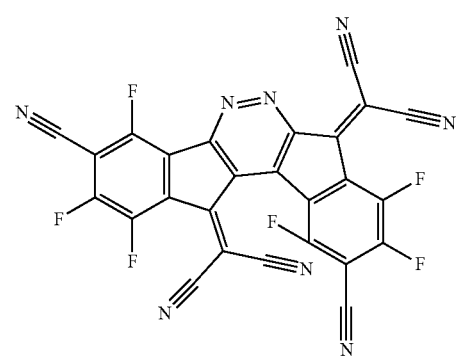
44
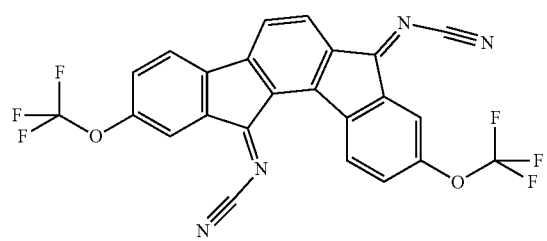
45
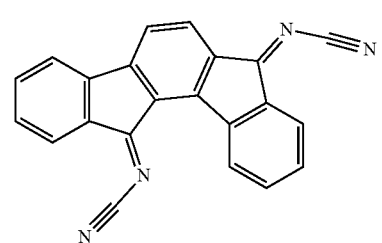
46
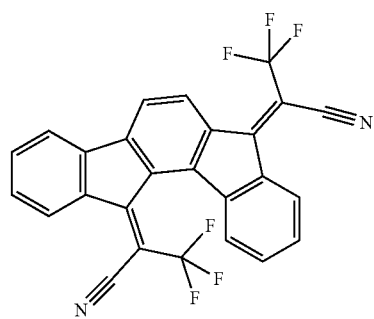
47
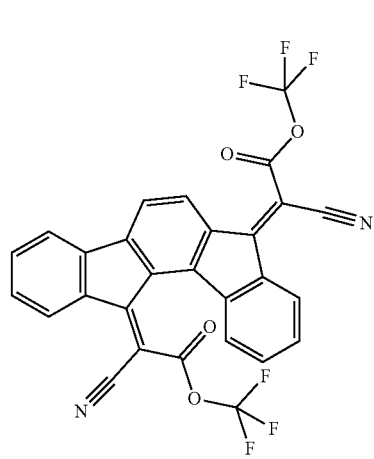
48
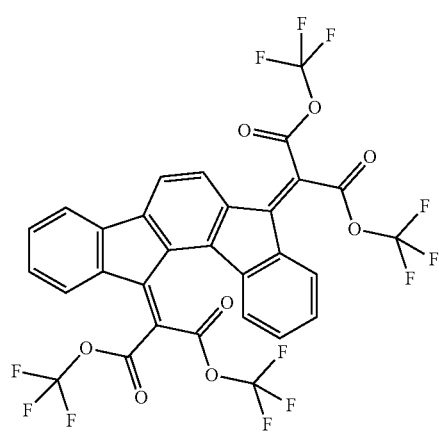
49
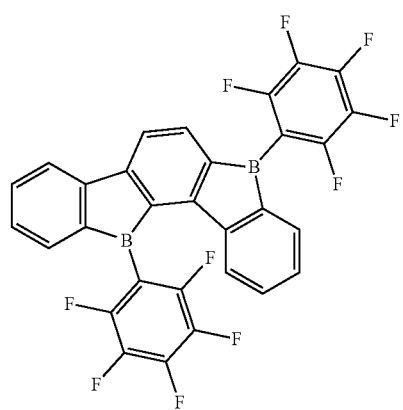
50

35
-continued
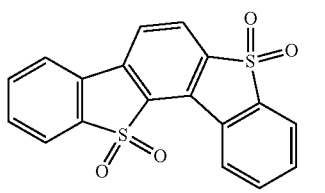
51
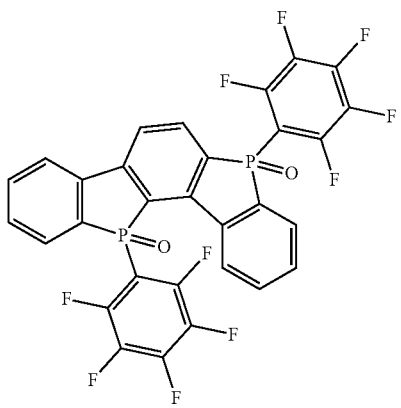
52
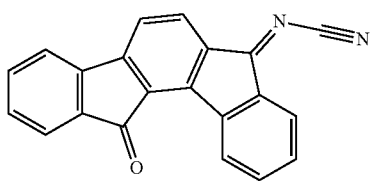
53
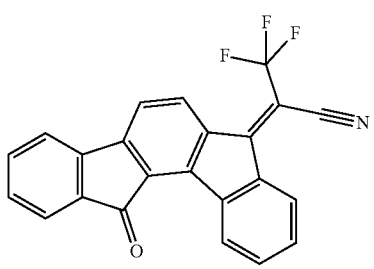
54
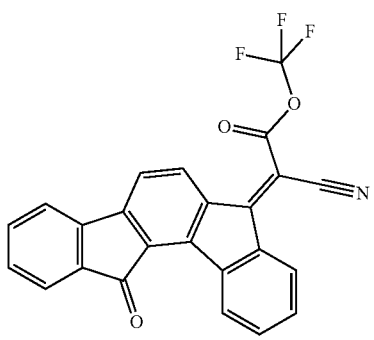
55
36
-continued
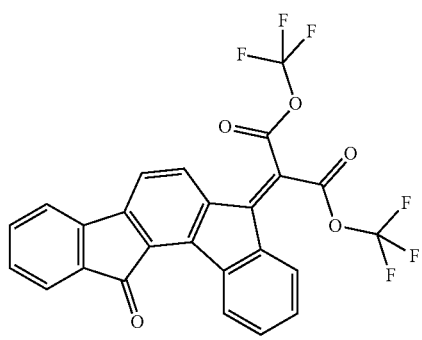
56
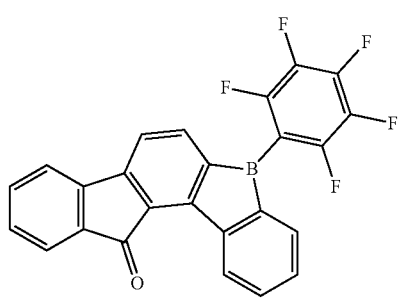
57
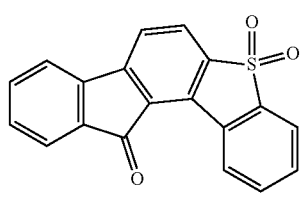
58
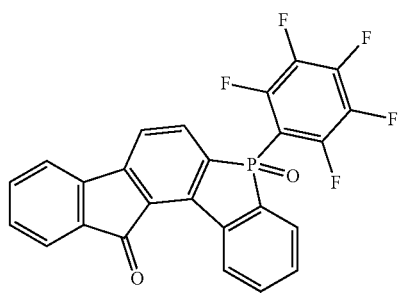
59
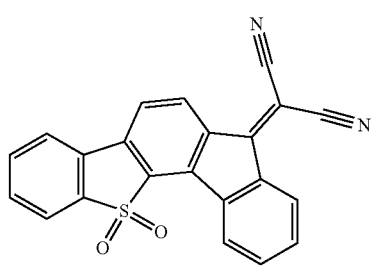
60

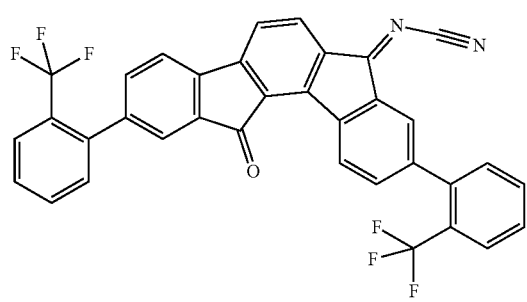
61
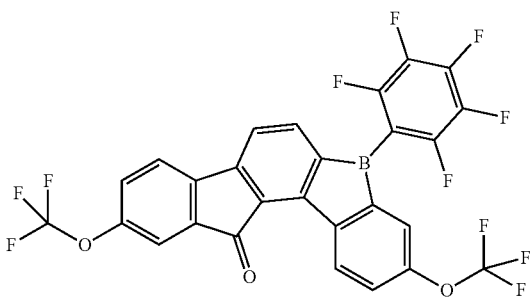
65
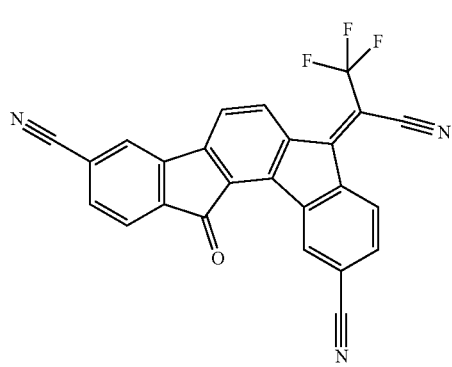
62
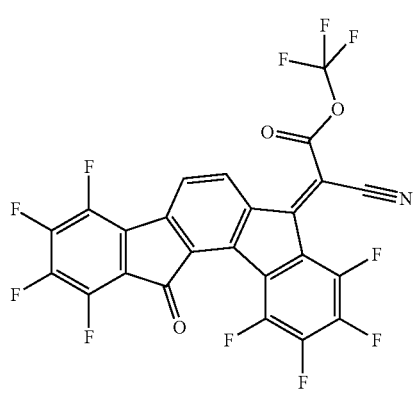
63
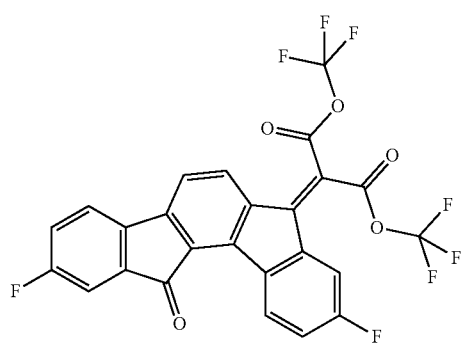
64
66
67
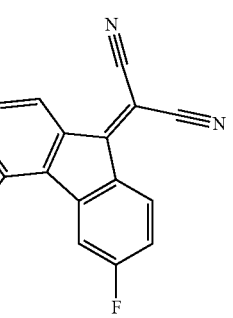
68

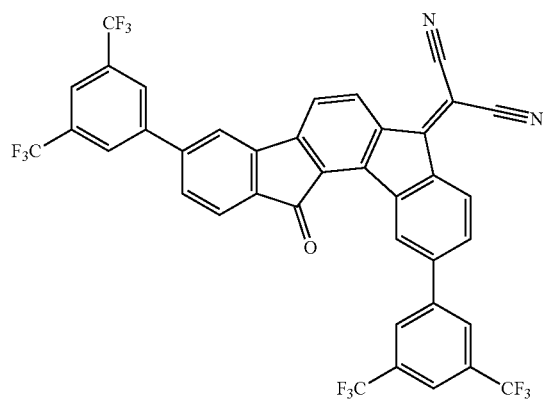

The compounds of the formula (1) can be prepared by known processes or reaction steps of organic chemistry.

A preferred process for the preparation of compounds of the formula (1) is shown below with Scheme 1 to Scheme 3:

Scheme 1

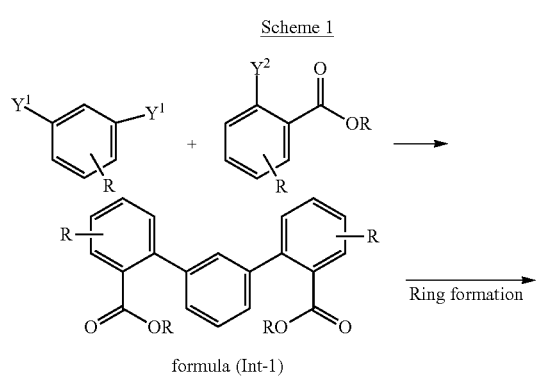

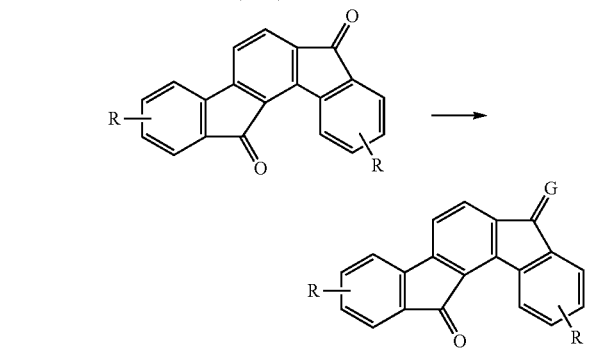

R: H or a radical
$Y^1$, $Y^2$: reactive groups (like Cl, Br, I, B(OR)$^2$)
G: Group replacing O (like C(CN)$_2$)

Scheme 2

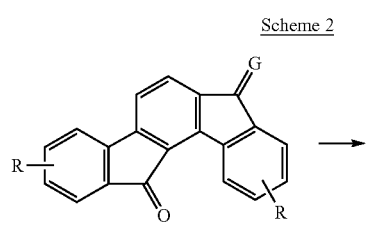

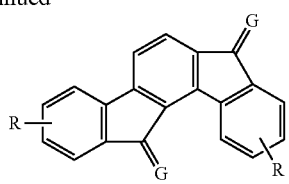

R : H or a radical
G: Group replacing O (like C(CN)$_2$)

Scheme 3

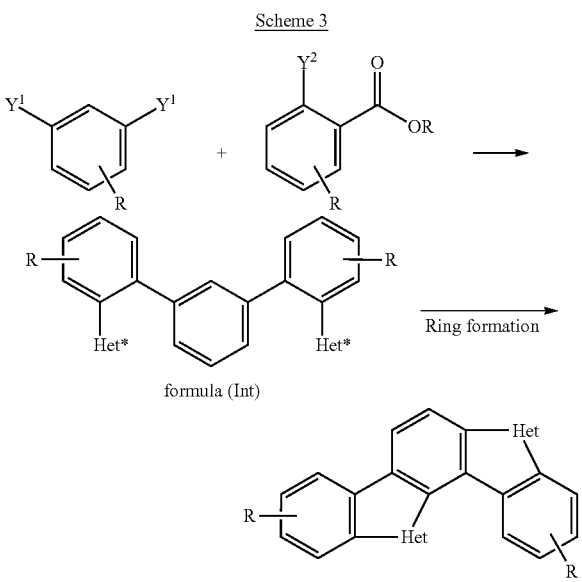

R: H or a radical
$Y^1$, $Y^2$: reactive groups (like Cl, Br, I, B(OR)$^2$)
Het*: precurseur for bridging group Het
Het: bridging group bonded via an heteroatom to the benzene groups represented in formula (Int)

Preferably, the process for the preparation of a compound according to the invention comprises the following steps:

a) Synthese of a terphenyl dicarboxylate derivative of formula (Int-1) according to the following reaction scheme:

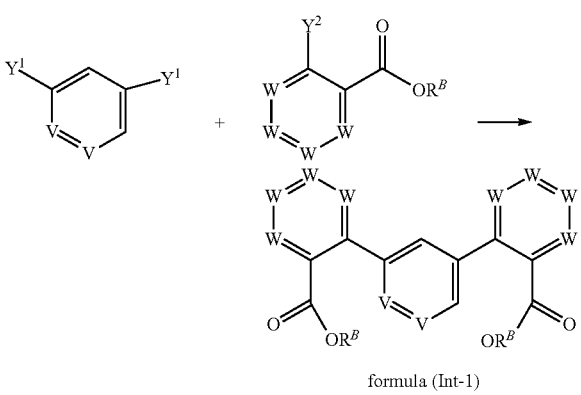

b) Synthese of a fluorenedione derivative of formula (Int-2) according to the following scheme:

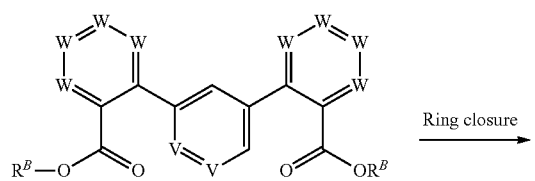

formula (Int-1)

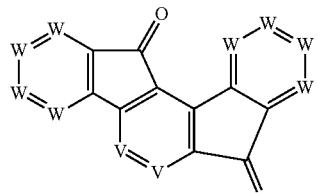

formula (Int-2)

c) Reaction of the compound of formula (Int-2) with a precursor X$^1$* of a group of one of the formulae (X-2) to (X-6);

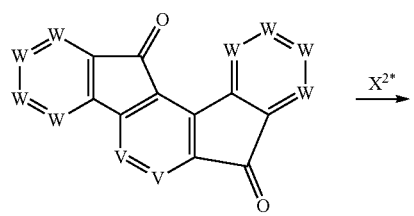

formula (Int-2)

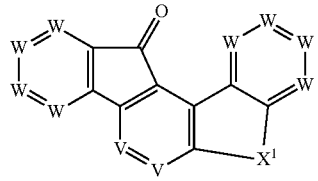

where
Y$^1$ and Y$^2$ are reactive group selected from Br, Cl, I, B(OR$^B$)$_2$;
R$^B$ is H, a straight-chain alkyl having 1 to 10 C atoms, where two substituents R$^B$ may form a monocyclic aliphatic ring system that may be substituted by an alkyl group having 1 to 3 C atoms;
X$^1$ is selected from a group of one of the formulae (X-2) to (X-6); and
V and W have the same meaning as above.

Optionally, step c) described above can be followed by step d) as follows:

d) Reaction of the compound obtained in step c) with a precursor X$^2$* of one of the group of formulae (X-2) to (X-6);

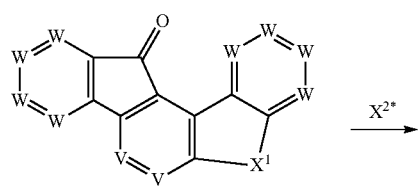

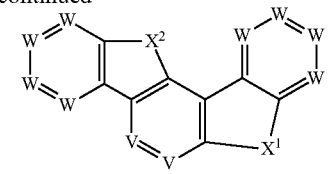

where
V and W have the same meaning as above; and
X$^1$ and X$^2$ are, identically or differently, selected from the groups of formulae (X-2) to (X-6).

Details on the processes indicated schematically above can be obtained from the working examples.

The person skilled in the art will be able to deviate from the processes indicated schematically above or modify them in order to obtain compounds of the formula (1), if this is necessary. This is carried out within the scope of the usual abilities of the person skilled in the art.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double or triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formula (1), where the bond(s) to the polymer, oligomer or dendrimer may be localised at any desired positions in formula (1) which are substituted by R, R$^1$ or R$^2$. Depending on the linking of the compound of the formula (1), the compound is part of a side chain of the oligomer or polymer or part of the main chain.

An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) may, for example, be linked via a trivalent or polyvalent group, for example via a trivalent or polyvalent aromatic or heteroaromatic group, to give a branched or dendritic oligomer or polymer.

The same preferences as described above for compounds of the formula (1) apply to the recurring units of the formula (1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 1992/18552), carbazoles (for example in accordance with WO 04/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxy-toluene, (−)-fenchone, 1,2,3,5-tetramethylbenzene, 1,2,4,5-tetramethyl-benzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (1) or at least one polymer, oligomer or dendrimer containing at least one unit of the formula (1), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (1) are suitable for use in electronic devices, in particular in organic electroluminescent devices (OLEDs). Depending on the substitution, the compounds are employed in various functions and layers.

The compound of the formula (1) can be employed in any function in the organic electroluminescent device, for example as hole-transporting material, as matrix material, as emitting material, or as electron-transporting material.

The invention therefore furthermore relates to the use of a compound of the formula (1) in an electronic device. The electronic device here is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (1). The electronic device is preferably selected from the devices indicated above. Particular preference is given to an organic electroluminescent device comprising anode, cathode and at least one emitting layer, characterised in that at least one organic layer comprises at least one compound of the formula (1).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, inter-layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device is preferably as follows: anode-hole-injection layer-hole-transport layer-emitting layer-electron-transport layer-electron-injection layer-cathode. It is not necessary for all of the said layers to be present, and further layers may additionally be present, for example an electron-blocking layer adjacent to the emitting layer on the anode side, or a hole-blocking layer adjacent to the emitting layer on the cathode side.

A hole-transport layer according to the present application is a layer with hole-transporting function, which is present between the anode and the emitting layer. In particular, it is a hole-transporting layer which is not a hole-injection layer or an electron-blocking layer. Hole-injection layers and electron-blocking layers in the sense of the present application are understood as specific embodiments of hole-transporting layers. A hole-injection layer is, in the case of a plurality of hole-transporting layers between the anode and the emitting layer, a hole-transporting layer which is adjacent to the anode or which is separated from the anode only through a single coating. An electron-blocking layer is, in the case of several hole-transporting layers between the anode and the emitting layer, a hole-transporting layer, which is adjacent to the emitting layer on the anode side.

The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue, green, yellow, orange or red light are used in the emitting layers. Particular preference is given to three-layer systems, i.e. systems having three emitting layers, where at least one of these layers preferably comprises at least one compound of the formula (1) and where the three layers exhibit blue, green, yellow, orange or red emission (for the basic structure see, for example, WO 2005/011013). It should be noted that, for the generation of white light, an emitter compound used individually which emits in a broad wavelength range may also be suitable instead of a plurality of emitter compounds emitting in colour. Alternatively and/or additionally, the compounds according to the invention may also be present in the hole-transport layer or in another layer in an organic electroluminescent device of this type. The various emitting layers may be directly adjacent to one another, or they may be separated from one another by non-emitting layers. According to a preferred embodiment of the invention, a white-emitting OLED is a so-called tandem OLED, i.e. two or more complete OLED layer sequences are present in the OLED, where the OLED layer sequences in each case comprise hole-transport layer, emitting layer and electron-transport layer, which are each separated from one another by a charge-generation layer.

In accordance with a preferred embodiment, the compound of formula (1) is employed as a p-dopant in a hole-transporting layer (for example a hole-injection layer, a hole-transport layer or an electron-blocker layer) in combination with one or more hole-transport materials. Suitable hole-transport materials which can be used in a hole-transport, hole-injection or electron-blocking layer in combination with a compound of formula (1) are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with EP 2875092, EP 2875699 and EP 2875004), spirodibenzopyranamines (for example in accordance with WO 2013/083216) and dihydroacridine derivatives (for example in accordance with WO 2012/150001).

When the compound of formula (1) is used as a p-dopant in a hole-transporting layer, the proportion of the compound of formula (1) in the mixture of the hole-transporting layer is between 0.1 and 50.0%, preferably between 0.5 and 20.0%, particularly preferably between 1.0 and 10.0%. Correspondingly, the proportion of the hole-transport material or hole-transport materials is between 50.0 and 99.9%, preferably between 80.0 and 99.5%, particularly preferably between 90.0 and 99.0%.

The specifications of the proportions in % are, for the purposes of the present application, taken to mean % by vol. if the compounds are applied from the gas phase and % by weight if the compounds are applied from solution.

The p-dopants are preferably distributed substantially uniformly in the p-doped layers. This can be achieved for example by co-evaporation of the p-dopant and of the hole-transport material matrix.

The compounds of formula (1) employed as a p-dopant in a layer can be employed in combination with other p-dopants.

Particularly preferred embodiments of p-dopants other than the compounds of formula (1) are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred p-dopants other than the compounds of formula (1) are quinodimethane compounds, azaindenofluorenediones, azaphenalenes, azatriphenylenes, $I_2$, metal halides, preferably transition metal halides, metal oxides, preferably metal oxides containing at least one transition metal or a metal of the 3 third main group, and transition metal complexes, preferably complexes of Cu, Co, Ni, Pd and Pt with ligands containing at least one oxygen atom as bonding site. Preference is also given to transition metal oxides as dopants, preferably oxides of rhenium, molybdenum and tungsten, particularly preferably $Re_2O_7$, $MoO3$, $WO_3$ and $ReO_3$.

Examples of suitable p-dopants other than the compounds of formula (1) are the compounds (D-1) to (D-13):

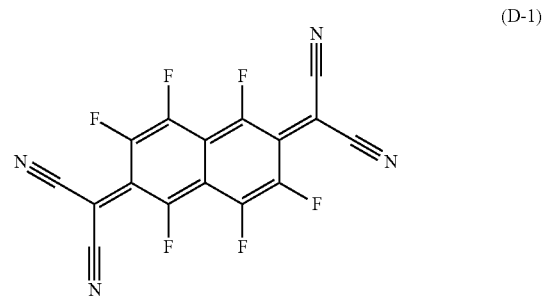

(D-1)

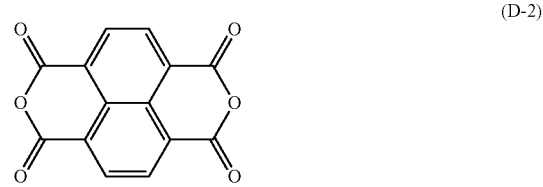

(D-2)

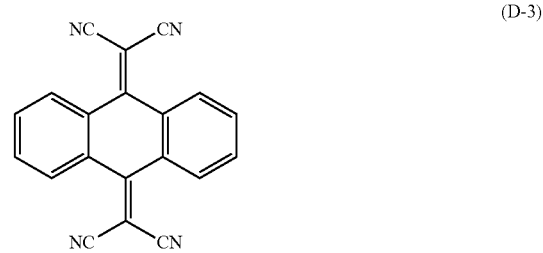

(D-3)

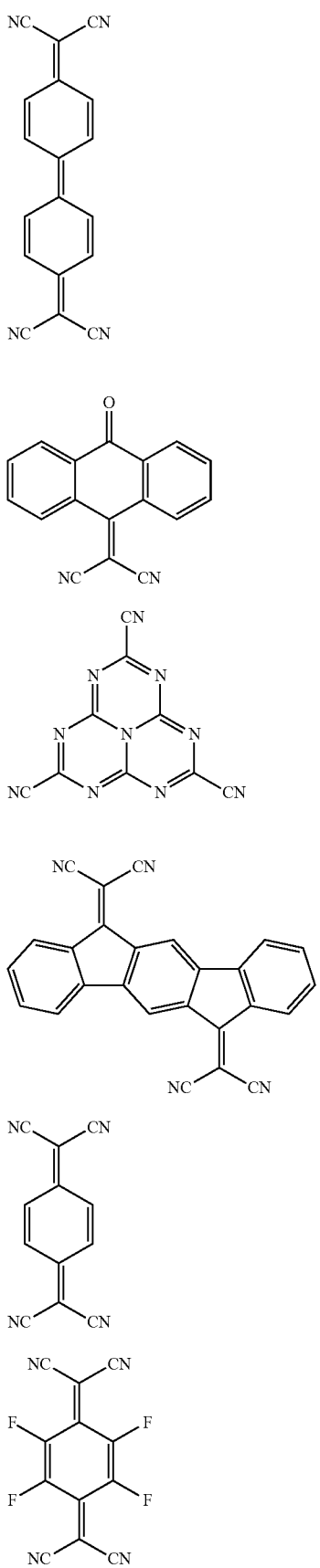
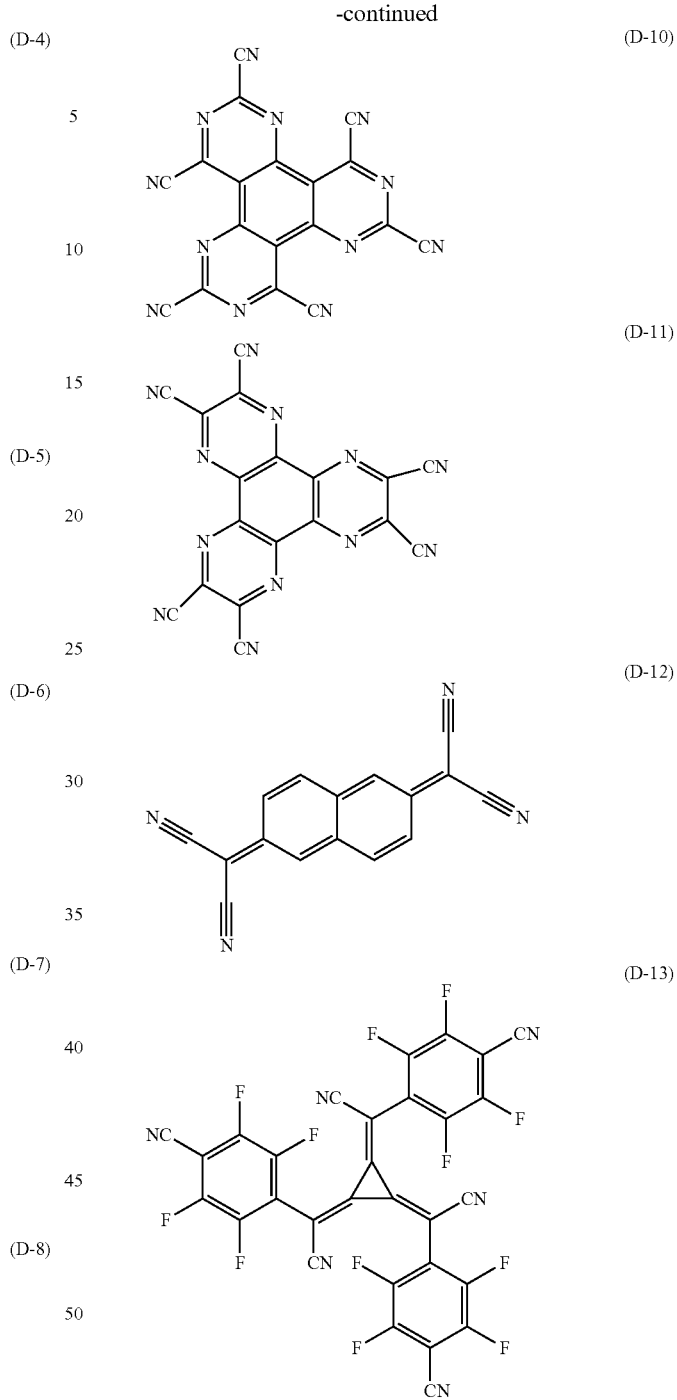

In accordance with another preferred embodiment, the compound of the formula (1) can be employed as a main compound, for example in a hole-transport layer, a hole-injection layer or an electron-blocking layer, either as a pure material, i.e. in a proportion of 100% or it can be employed in combination with one or more further compounds. When it is used in combination with one or more further compounds, the proportion of the compound of formula (1) is then preferably between 50.0 and 99.9%, preferably between 80.0 and 99.5%, particularly preferably between 90.0 and 99.0%.

When the compound of formula (1) is employed as a main compound (in a proportion of from 50 to 100%, preferably from 80 to 100%, very preferably from 90 to 100%, particularly preferably from 99 to 100%) in a hole-injection layer, then the hole-injection layer has a thickness layer of from 0.5 to 50 nm, preferably from 1 to 20 nm, very preferably 1 to 10 nm and particularly preferably 1 to 5 nm.

It is furthermore preferred for the electronic device to have a plurality of hole-transporting layers between the anode and the emitting layer. The case may occur that all these layers comprise a compound of the formula (1), or that only individual layers thereof comprise a compound of the formula (1).

Generally preferred classes of material for use as corresponding functional materials in the organic electroluminescent devices according to the invention are indicated below.

Suitable phosphorescent emitting compounds are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitting compounds used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of the phosphorescent emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094962, WO 2014/094961, WO 2014/094960 or WO 2016/124304. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Preferred fluorescent emitters, besides the compounds according to the invention, are selected from the class of the arylamines. An arylamine in the sense of this invention is taken to mean a compound which contains three substituted or unsubstituted aromatic or heteroaromatic ring systems bonded directly to the nitrogen. At least one of these aromatic or hetero-aromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysene-diamines are defined analogously thereto, where the diarylamino groups are preferably bonded to the pyrene in the 1-position or in the 1,6-position.

Further preferred emitters are indenofluorenamines or indenofluorene-diamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328. Preference is likewise given to the pyrenarylamines disclosed in WO 2012/048780 and WO 2013/185871. Preference is likewise given to the benzoindenofluorenamines disclosed in WO 2014/037077, to the benzofluorenamines disclosed in WO 2014/106522, to the benzoindenofluorenes disclosed in WO 2014/111269 and WO 2017/036574, to the phenoxazines disclosed in WO 2017/028940 and WO 2017/028941 and to the fluorene derivatives disclosed in WO 2016/150544.

Preferred matrix materials for use in combination with fluorescent emitting compounds are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another. Preference is likewise given to anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, to pyrene derivatives disclosed in EP 1749809, EP 1905754 and US 2012/0187826, to benzanthracenyl-anthracene derivatives disclosed in WO 2015/158409, to indenobenzofurans disclosed in WO 2017/025165 and to phenanthryl-anthracenes disclosed in WO 2017/036573.

Preferred matrix materials for use in combination with phosphorescent emitting are aromatic ketones, aromatic phosphine oxides or aromatic sulfoxides or sulphones, for example according to WO 2004/013080, WO 2004/093207, WO 2006/005627 or WO 2010/006680, triarylamines, carbazole derivatives, for example CBP (N, N-biscarbarbolyl-biphenyl) or the carbazoles derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boron esters, for example according to WO 2006/117052, triazine derivatives, for example according to WO 2010/015306, WO 2007/063754 or WO 2008/056746, zink complexes, for example according to EP 652273 or WO 2009/062578, diazasilole derivatives or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Examples of preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with WO 2014/015937, WO 2014/015938, WO 2014/015935 and WO 2015/082/056), spirodibenzopyranamines (for example in accordance with WO 2013/083216), dihydroacridine derivatives (for example in accordance with WO 2012/150001), spirodibenzofurans and spirodibenzothiophenes, for example according to WO 2015/022051 and WO 2016/102048 and WO 2016/131521, phenanthrene diarylamines, for example according to WO 2015/131976, spiro-tribenzotropolones, for example according to WO 2016/087017, spirobifluorenes with meta-phenyldiamine groups, for example according to WO 2016/078738, spirobisacridines, for example according to WO 2015/158411, xanthene diarylamines, for example according to WO 2014/072017, and 9,10-dihydroanthracene spiro compounds having diarylamino groups according to WO 2015/086108.

Concerning the electron-transport layer, the materials that are known or used as electron-transport materials according to the prior art can all be employed in the electron-transport layer. Particularly suitable as electron-transport materials are the following compounds: aluminum complexes, for example Alq3, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above compounds as described in JP 2000/053957, WO 2003/060956, WO 2004/028217, WO 2004/080975 and WO 2010/072300.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

WORKING EXAMPLES

A) Synthesis Examples

Example 1 (E1) 2-(12-oxo-2,9-bis(trifluoromethoxy)indeno[1,2-a]fluoren-7-ylidene)malononitrile a) Dimethyl 4,4''-bis(trifluoromethoxy)-[1,1':3',1''-terphenyl]-2,2''-dicarboxylate

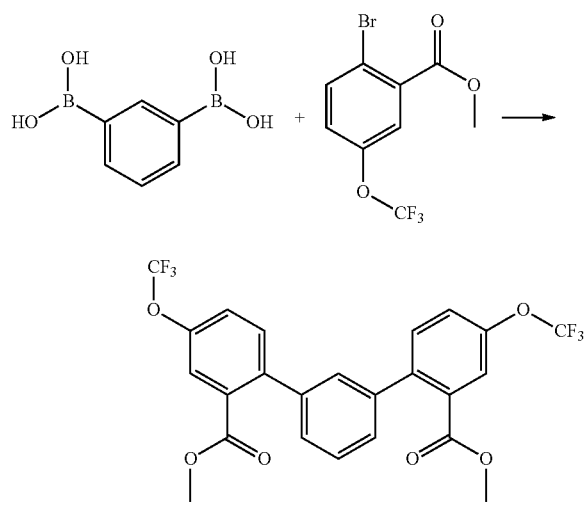

Methyl 2-bromo-5-(trifluoromethoxy)benzoate (63.5 g, 212.4 mmol), 1,3-phenylenediboronic acid (16.0 g, 96.5 mmol) and $K_3PO_4$ (88.9 g, 386.1 mmol) are dissolved in toluene (700 ml)/ethanol (420 ml)/water (280 ml) under argon. The solution is degassed and $Pd(PPh_3)_4$ (5.57 g, 4.83 mmol) is added. The mixture is heated up to 60° C. over night. After cooling to room temperature, the solution is poured into water (300 ml) with vigorous stirring. The layers are separated and the aqueous layer is extracted with toluene (2×100 ml) and dichloromethane (100 ml). The combined organic layers are washed with brine (150 ml) and dried over $MgSO_4$. The solvent is evaporated in vacuo. The crude product is purified via silica column chromatography using ethyl acetate/heptane (1:4) as eluent. The product is obtained as yellow glue (51.3 g, quant. with some impurities).

1H NMR (CDCl$_3$, 500 MHz): δ=3.69 (s, 6H, COOC$\underline{H}_3$), 7.21-7.22 (m, 1H, H-2'), 7.30 (dd, 2H, $^3$J=7.3 Hz, $^4$J=1.7 Hz, H-5,5"), 7.37-7.40 (m, 2H, H-4',6'), 7.41-7.45 (m, 3H, H-6,6", H-5), 7.71 (d, 2H, $^4$J=1.6 Hz, H-3,3") ppm GC-MS (EI, 70 eV)=514 (60%), 451 (100%), 423 (25%), 326 (20%)

b) 2,9-bis(trifluoromethoxy)indeno[1,2-a]fluorene-7,12-dione

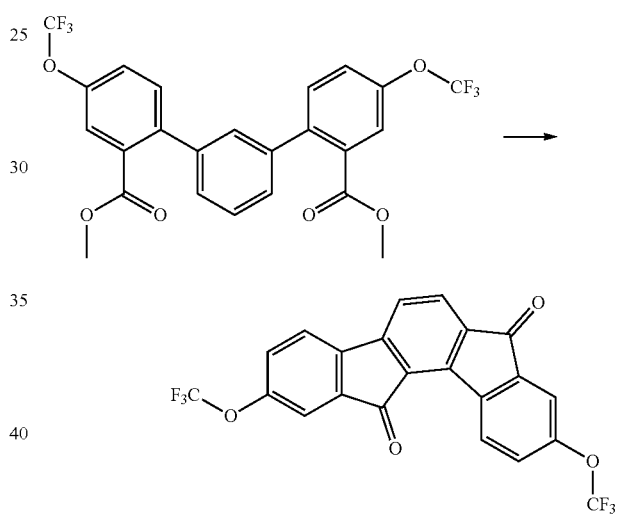

Dimethyl 4,4''-bis(trifluoromethoxy)-[1,1':3',1''-terphenyl]-2,2''-dicarboxylate (51.3 g, 99.8 mmol) is dissolved in conc. $H_2SO_4$ (400 ml). The mixture is stirred at room temperature for 1 h, then heated up to 50° C. over night. The temperature is increased to 70° C. until TLC shows complete consumption of the starting material. After cooling to room temperature, the reaction mixture is poured into iced water. A voluminous yellow precipitate is formed. The solid is filtered off and is washed with water, ethanol and heptane. The crude material is dried in vacuo at 60° C. over night. It is filtered over silica using DCM and DCM+10% methanol as eluent. The crude product (39.55 g, 87.8 mmol, 88%) is used in the next reaction without further purification.

TLC: Rf(product)=0.55, (silica, DCM/heptane 3:1)

1H NMR (CDCl$_3$, 500 MHz): δ=7.44 (dd, 1H, $^3$J=8.2 Hz, $^4$J=1.5 Hz, H-3), 7.48 (dd, 1H, $^3$J=8.2 Hz, $^4$J=1.5 Hz, H-10), 7.54 (d, 1H, $^3$J=7.3 Hz, H-5), 7.59-7.60 (m, 1H, H-1), 7.63-7.64 (m, 1H, H-8), 7.69 (d, 1H, $^3$J=8.2 Hz, H-4), 7.88 (d, 1H, $^3$J=7.4 Hz, H-6), 8.95 (d, 1H, $^3$J=8.2 Hz, H-11) ppm GC-MS (EI, 70 eV)=450 (100%), 325 (40%), 200 (15%)

c) 2-(12-oxo-2,9-bis(trifluoromethoxy)indeno[1,2-a]fluoren-7-ylidene)malononitrile (E1)

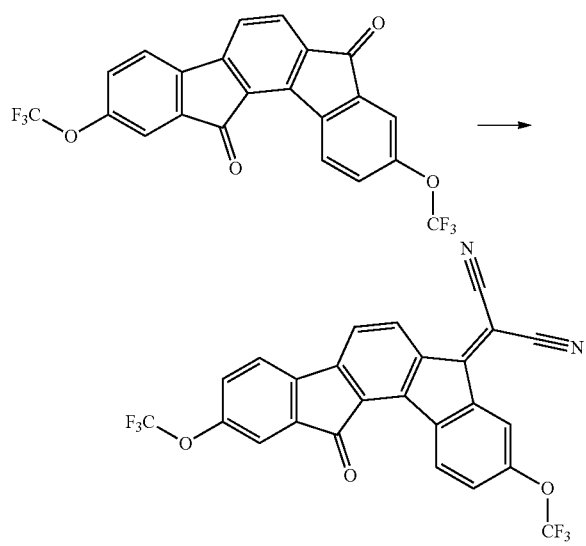

Crude material of 2,9-bis(trifluoromethoxy)indeno[1,2-a]fluorene-7,12-dione (39.55 g, 87.8 mmol) is dissolved in pyridine (1500 ml) under argon. Malononitrile (34.8 g, 527 mmol) is added and the reaction mixture is heated up to 65° C. over night. After cooling to room temperature the reaction mixture is diluted with dichloromethane and 1 M HCl. The layers are separated and the aqueous layer is extracted with dichloromethane. The combined organic layers are dried over MgSO$_4$ and the solvent is removed in vacuo. The crude product (63.3 g) is obtained as red solid. The material is further purified via silica column chromatography using heptane and dichloromethane (1:2) as eluent. The isolated product fraction is recrystallized from heptane/dichloromethane. E1 (6.3 g, 12.6 mmol, 14%) is obtained as fluffy orange solid. The material is sublimed for further purification.

TLC: Rf(E1)=0.46, (silica, ethyl acetate/heptane 1:2)

1H NMR (CDCl$_3$, 500 MHz): δ=7.46 (dd, 1H, $^3J$=8.1 Hz, $^4J$=1.5 Hz, H-3), 7.51 (dd, 1H, $^3J$=8.5 Hz, $^4J$=1.1 Hz, H-10), 7.55 (d, 1H, $^3J$=8.1 Hz, H-5), 7.62 (s, 1H, H-1), 7.71 (d, 1H, $^3J$=8.5 Hz, H-4), 8.35 (s, 1H, H-8), 8.66 (d, 1H, $^3J$=8.0 Hz, H-6), 9.18 (d, 1H, $^3J$=8.4 Hz, H-11) ppm MS (ESI+): m/z=499 (M+H$^+$)

Example 2 (E2) 2-(12-oxo-2,9-bis(trifluoromethoxy)indeno[1,2-a]fluoren-7-ylidene)malononitrile

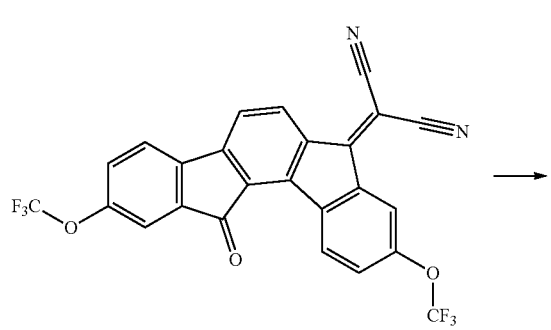

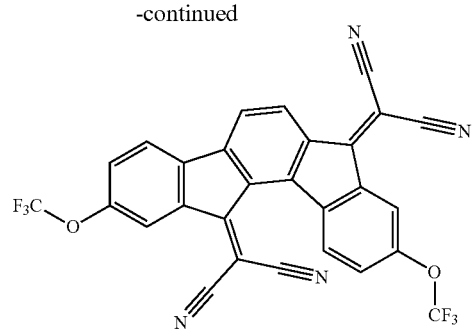

E1 (50 mg, 0.10 mmol) and malononitrile (0.13 g, 2.01 mmol) are dissolved in pyridine (4 ml). The reaction mixture is heated to 100° C. for 24 h. After cooling to room temperature, aqueous HCl (1 M) is added. The red precipitate is filtered off and is washed with water, little DCM and heptane.

E2 is obtained as red powder.

TLC: Rf(E2)=0.05, (silica, ethyl acetate/heptane 1:2)

MS (EI+): m/z=546 (M$^{*+}$)

Examples 3 to 16 (E3 to E-16)

Following compounds can be obtained in analogy by using the same synthetic procedure as described for E1 (E3-E9) and E2 (E10-E16):

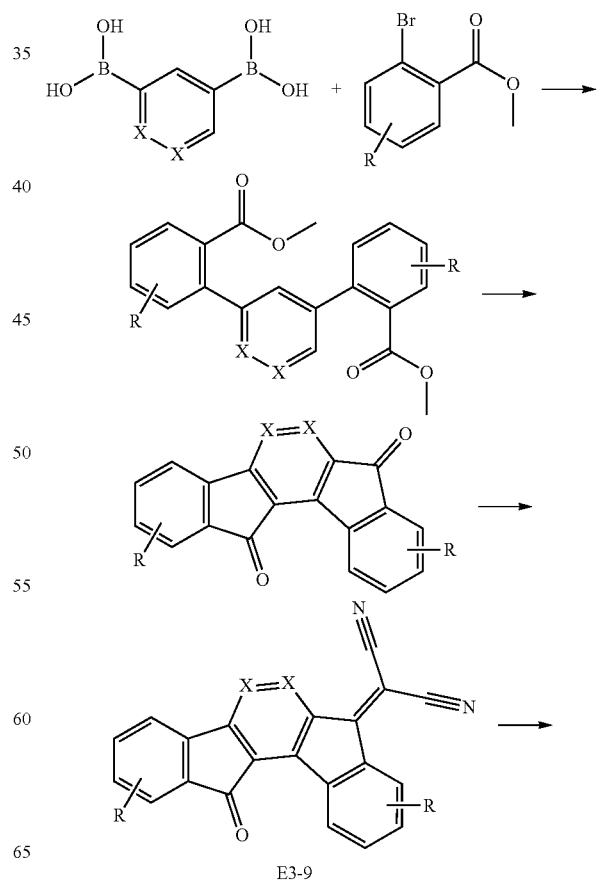

E3-9

E10-16
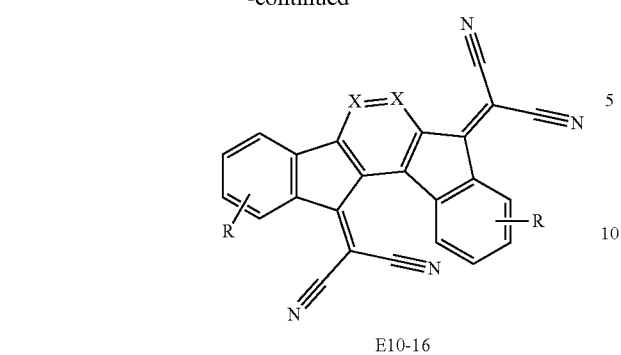
E3
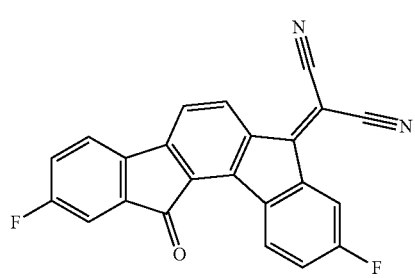
E4
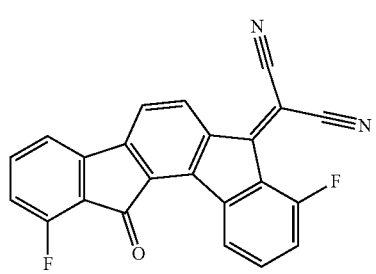
E5
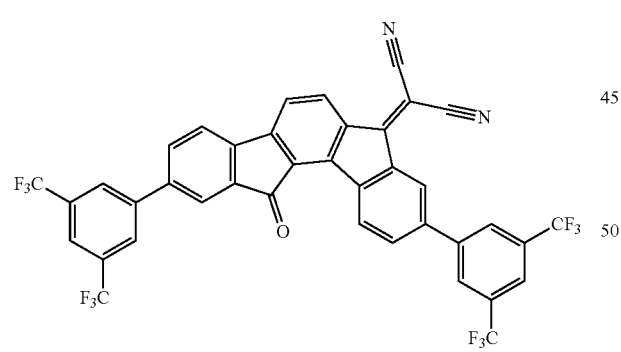
E6
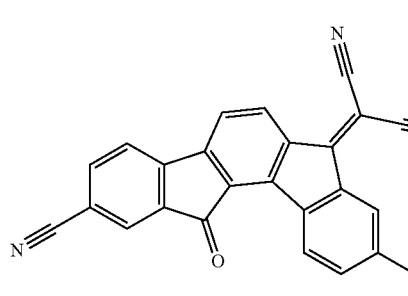
E7
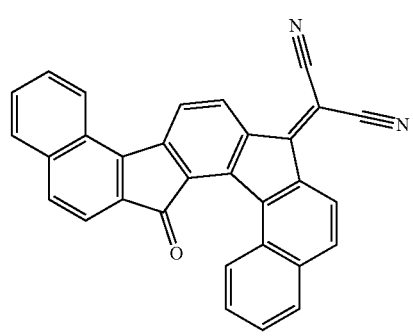
E8
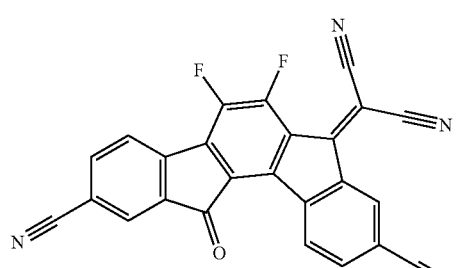
E9
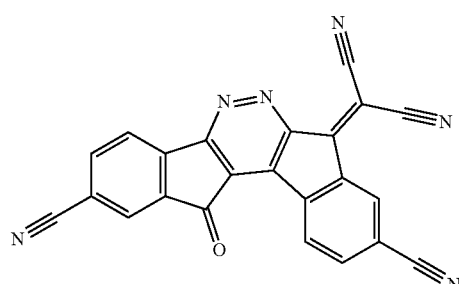
E10
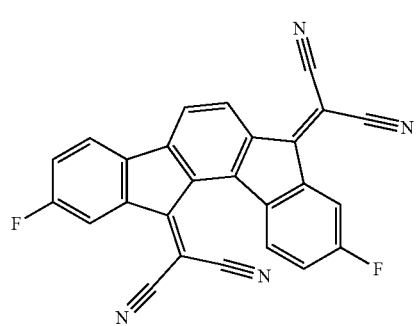
E11
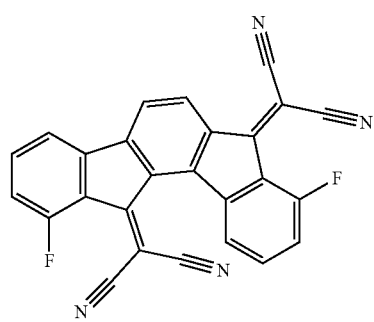

-continued

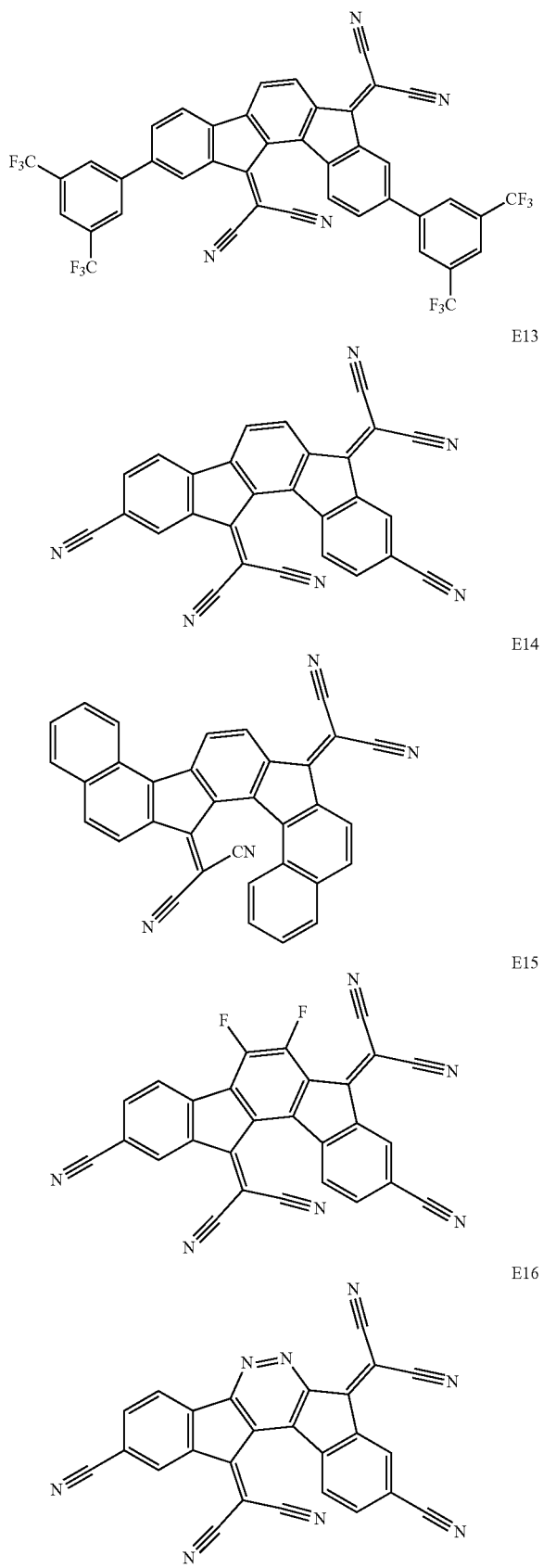

B) Device Examples

The data for various devices are presented in Examples below (see Tables 1 to 2). The substrates used are glass plates coated with structured ITO (indium tin oxide) with a thickness of 50 nm.

Freshly cleaned substrates are transferred into the evaporation tool. Here the substrates are either preconditioned with oxygen plasma for 130 s and afterwards treated with argon plasma for 150 s (Oxygen_Argon) or only preconditioned with oxygen plasma for 130 s (Oxygen).

Afterwards several organic layers are deposited by physical vapour deposition.

The thickness of the layers is determined by reference experiments, where thick layers of roughly 100 nm organic material are deposited. The thickness is measured during the evaporation by a thin-film thickness monitor, based on quartz crystal microbalance, e.g. Inficon. The organic layer is protected by evaporation of a thin aluminium film on top. Then the real thickness of the organic layer is measured by a surface profiler, e.g. K-LA-Tencor P7. The tooling factor of the thin-film monitor is adapted in a way that the film thickness of the surface profiler and the thin film monitor is the same.

The devices basically have the following layer structure: substrate/hole-injection layer (HIL)/hole-transport layer (HTL) and finally a cathode. The cathode is formed by an aluminium layer with a thickness of 100 nm. The precise structure of the devices is shown in table 1. The materials required for the production of the devices are shown in table 5.

All materials are applied by thermal vapour deposition in a vacuum chamber. An expression such as HTM1: HIM1 (5%) here means that material HTM1 is present in the layer in a proportion by volume of 95% and HIM1 is present in the layer in a proportion of 5%. Analogously, other layers may also consist of a mixture of two or more materials.

The OLEDs are characterised by standard methods. For this purpose, the electroluminescence spectra and the external quantum efficiency (EQE, measured in percent) as a function of the luminous density, calculated from current/voltage/luminous density characteristic lines (IUL characteristic lines) assuming Lambert emission characteristics. The expression EQE @10 $mA/cm^2$ denotes the external quantum efficiency at an operating current density of 10 $mA/cm^2$. LT90 @ 60 $mA/cm^2$ is the lifetime until the OLED has dropped from its initial luminance of i.e. 5000 $cd/m^2$ to 90% of the initial intensity, i.e. to 4500 $cd/m^2$ without using any acceleration factor. The data for the various OLEDs containing inventive and comparative materials are summarised in table 2 and 4.

| Ex. | Plasma | HIL Thickness/ nm | HTL Thickness/ nm | Cathode Thickness/ mm |
|---|---|---|---|---|
| V1 | Oxygen_Argon | HATCN 5 nm | HTM1 100 nm | Al 100 nm |

| Ex. | Plasma | HIL Thickness/nm | HTL Thickness/nm | Cathode Thickness/nm |
|---|---|---|---|---|
| V2 | Oxygen | — | HTM1 100 nm | Al 100 nm |
| V3 | Oxygen | — | HTM2 100 nm | Al 100 nm |
| V4 | Oxygen | — | HTM3 100 nm | Al 100 nm |
| V5 | Oxygen | — | HTM4 100 nm | Al 100 nm |
| E1 | Oxygen_Argon | HIM1 5 nm | HTM1 100 nm | Al 100 nm |
| E2 | Oxygen_Argon | HIM1 2 nm | HTM1 100 nm | Al 100 nm |
| E3 | Oxygen_Argon | HIM1 2 nm | HTM2 100 nm | Al 100 nm |
| E4 | Oxygen_Argon | HIM1 2 nm | HTM3 100 nm | Al 100 nm |
| E5 | Oxygen_Argon | HIM1 3 nm | HTM3 100 nm | Al 100 nm |
| E6 | Oxygen_Argon | HIM1 4 nm | HTM3 100 nm | Al 100 nm |
| E7 | Oxygen_Argon | HIM1 5 nm | HTM3 100 nm | Al 100 nm |
| E8 | Oxygen_Argon | HIM1 2 nm | HTM4 100 nm | Al 100 nm |
| E9 | Oxygen_Argon | HIM1 3 nm | HTM4 100 nm | Al 100 nm |
| E10 | Oxygen_Argon | HIM1 4 nm | HTM4 100 nm | Al 100 nm |
| E11 | Oxygen_Argon | HIM1 5 nm | HTM4 100 nm | Al 100 nm |
| E12 | Oxygen | HIM1 2 nm | HTM1 100 nm | Al 100 nm |
| E13 | Oxygen | HIM1 3 nm | HTM1 100 nm | Al 100 nm |
| E14 | Oxygen | HIM1 4 nm | HTM1 100 nm | Al 100 nm |
| E15 | Oxygen | HIM1 5 nm | HTM1 100 nm | Al 100 nm |
| E16 | Oxygen | HIM1 2 nm | HTM2 100 nm | Al 100 nm |
| E17 | Oxygen | HIM1 3 nm | HTM2 100 nm | Al 100 nm |
| E18 | Oxygen | HIM1 4 nm | HTM2 100 nm | Al 100 nm |
| E19 | Oxygen | HIM1 5 nm | HTM2 100 nm | Al 100 nm |
| E20 | Oxygen | HIM1 2 nm | HTM3 100 nm | Al 100 nm |
| E21 | Oxygen | HIM1 3 nm | HTM3 100 nm | Al 100 nm |
| E22 | Oxygen | HIM1 4 nm | HTM3 100 nm | Al 100 nm |
| E23 | Oxygen | HIM1 5 nm | HTM3 100 nm | Al 100 nm |
| E24 | Oxygen | HIM1 2 nm | HTM4 100 nm | Al 100 nm |
| E25 | Oxygen | HIM1 3 nm | HTM4 100 nm | Al 100 nm |
| E26 | Oxygen | HIM1 4 nm | HTM4 100 nm | Al 100 nm |
| E27 | Oxygen | HIM1 5 nm | HTM4 100 nm | Al 100 nm |

| Ex. | U @ 10 mA/cm$^2$ [V] | U @ 100 mA/cm$^2$ [V] |
|---|---|---|
| V1 | 1.5 | 2.3 |
| V2 | 8.1 | 11.1 |
| V3 | 10.8 | 14.5 |
| V4 | 7.1 | 9.5 |
| V5 | 5.8 | 8.2 |
| E1 | 1.8 | 5.4 |
| E2 | 1.8 | 3.4 |
| E3 | 2.9 | 6.1 |
| E4 | 1.4 | 2.3 |
| E5 | 1.4 | 2.3 |
| E6 | 1.4 | 2.4 |
| E7 | 1.4 | 3.0 |
| E8 | 1.4 | 2.5 |
| E9 | 1.4 | 2.5 |
| E10 | 1.4 | 2.4 |
| E11 | 1.6 | 3.6 |
| E12 | 1.5 | 2.3 |
| E13 | 1.5 | 2.1 |
| E14 | 1.5 | 2.1 |
| E15 | 1.5 | 2.2 |
| E16 | 1.7 | 2.5 |
| E17 | 1.7 | 2.7 |
| E18 | 1.7 | 2.5 |
| E19 | 1.7 | 2.7 |
| E20 | 1.4 | 2.3 |
| E21 | 1.4 | 2.3 |
| E22 | 1.4 | 2.2 |
| E23 | 1.4 | 2.3 |
| E24 | 1.4 | 2.8 |
| E25 | 1.3 | 2.2 |
| E26 | 1.3 | 2.2 |
| E27 | 1.4 | 2.5 |

| Ex. | HIL Thickness/nm | HTL Thickness/nm | EBL Thickness/nm | EML Thickness/nm | ETM Thickness/nm | Cathode Thickness/nm |
|---|---|---|---|---|---|---|
| E28 | HIM1 3 nm | HTM3 175 nm | HTM1 10 nm | SMB; SEB (3%) 20 nm | ETM; LiQ (50%) 30 | Al 100 nm |

| Ex. | U @ 10 mA/cm$^2$ [V] | EQE @ 10 mA/cm$^2$ [%] | LT90 @ 60 mA/cm$^2$ h |
|---|---|---|---|
| E28 | 4.0 | 6.0 | 140 |

TABLE 5
Structures of the materials used
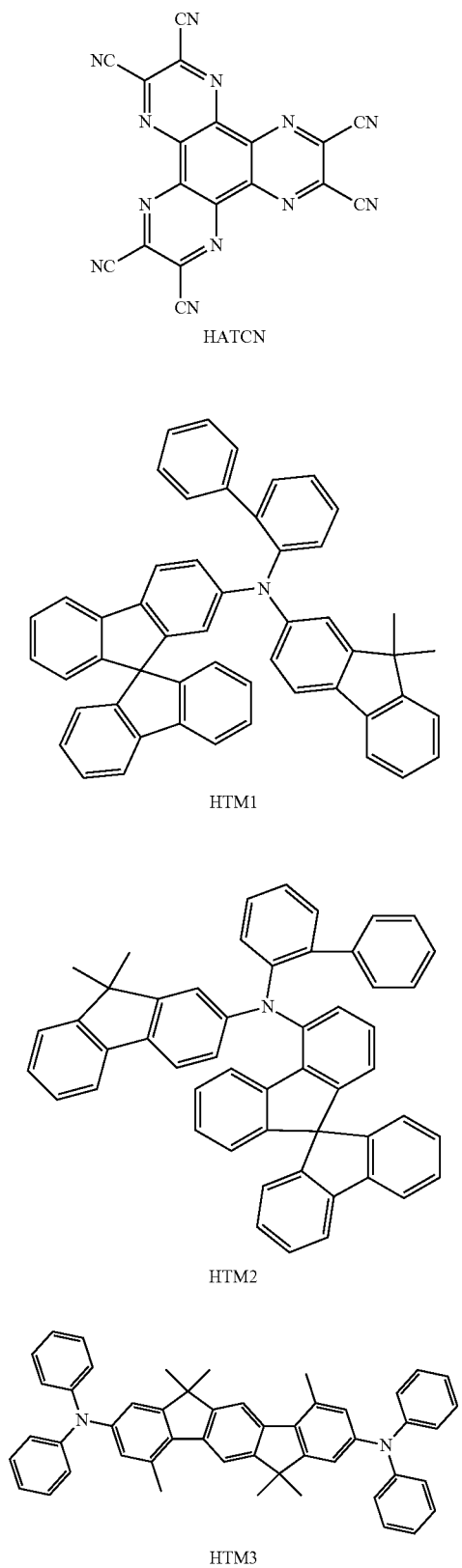
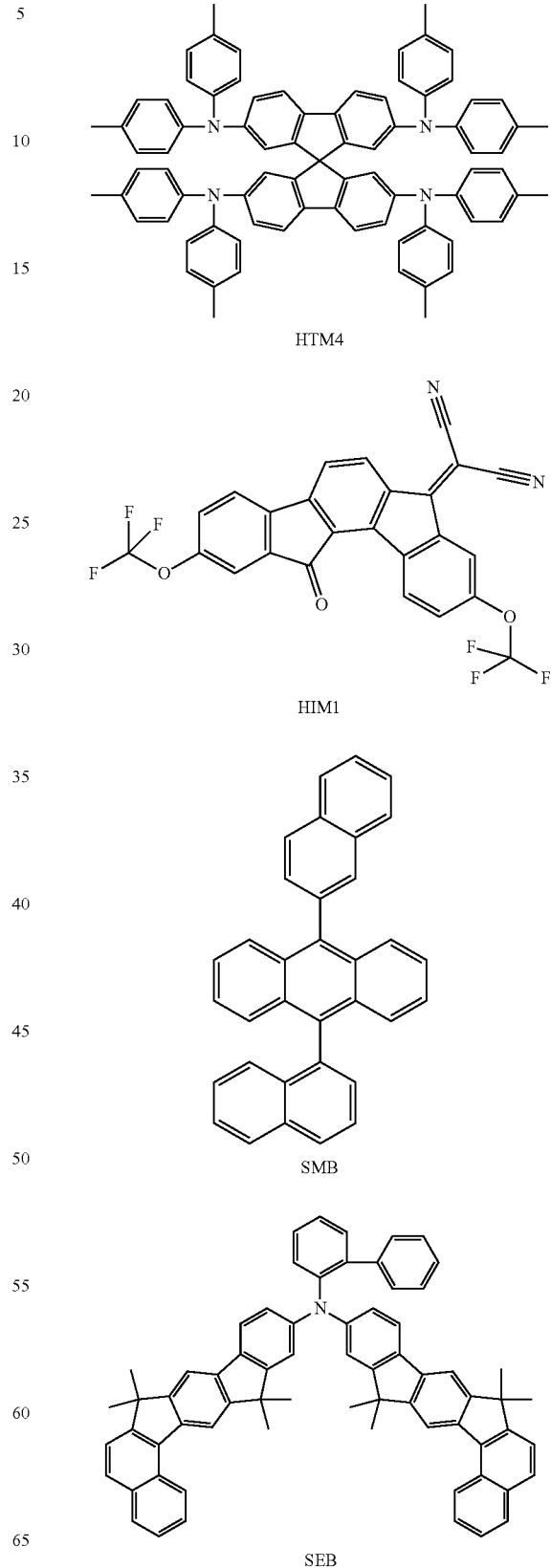

TABLE 5-continued

Structures of the materials used

ETM

LiQ

Examples

Devices with the structures shown in table 1 are produced. Table 2 shows the performance data of the examples described. The devices are hole-only devices in which HATCN and HIM1 are used as the hole injection layer (HIL). It can be shown, that very low voltages can be obtained with thin layers of HIM1, also in combination with deeper HOMO level HTMs, such as HTM2.

Furthermore, it can be shown that HIM1 also gives very low voltage, good efficiency and good lifetime in a blue device (E28).

The invention claimed is:

1. An organic electroluminescent device (OLED) comprising a compound of the formula (2A),

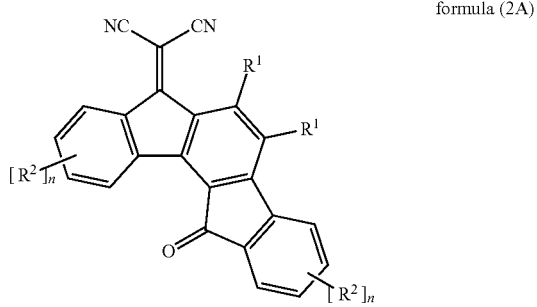

formula (2A)

where the following applies to the symbols and indices used:

$R^1$ stands on each occurrence, identically or differently, for H, D, F, CN, a straight-chain alkyl groups having 1 to 10 C, where one or more H atoms may be replaced by D or F;

$R^2$ stands on each occurrence, identically or differently, from the group consisting of F, CN, a straight-chain alkyl, alkoxy or thioalkyl groups having 1 to 20 C atoms or a branched or a cyclic alkyl, alkoxy or thioalkyl groups having 3 to 20 C atoms, each of which may be substituted by one or more radicals $R^3$, where in each case one or more non-adjacent $CH_2$ groups may be replaced by $R^3C=CR^3$, C≡C, C=O, P(=O)($R^3$), SO, $SO_2$, O, S or $CONR^3$ and where one or more H atoms may be replaced by D or F, an aromatic or heteroaromatic ring systems having 5 to 30 aromatic ring atoms, which may in each case be substituted by one or more radicals $R^3$, or an aryloxy groups having 5 to 30 aromatic ring atoms, which may be substituted by one or more radicals $R^3$;

$R^3$ stands on each occurrence, identically or differently, for H, D, F, Cl, Br, I, CHO, CN, N(Ar)$_2$, C(=O)Ar, P(=O)(Ar)$_2$, S(=O)Ar, S(=O)$_2$Ar, NO$_2$, Si($R^4$)$_3$, B(O$R^4$)$_2$, OSO$_2R^4$, a straight-chain alkyl, alkoxy or thioalkyl groups having 1 to 40 C atoms or branched or cyclic alkyl, alkoxy or thioalkyl groups having 3 to 40 C atoms, each of which may be substituted by one or more radicals $R^4$, where in each case one or more non-adjacent $CH_2$ groups may be replaced by $R^4C=CR^4$, C≡C, Si($R^4$)$_2$, Ge($R^4$)$_2$, Sn($R^4$)$_2$, C=O, C=S, C=Se, P(=O)($R^4$), SO, SO$_2$, O, S or $CONR^4$ and where one or more H atoms may be replaced by D, F, Cl, Br, I, CN or NO$_2$, an aromatic or heteroaromatic ring systems having 5 to 60 aromatic ring atoms, which may in each case be substituted by one or more radicals $R^4$, or an aryloxy group having 5 to 60 aromatic ring atoms, which may be substituted by one or more radicals $R^4$, where two adjacent substituents $R^3$ may form a mono- or polycyclic, aliphatic ring system or aromatic ring system, which may be substituted by one or more radicals $R^4$;

$R^4$ stands on each occurrence, identically or differently, for H, D, F, Cl, Br, I, CN, a straight-chain alkyl, alkoxy or thioalkyl groups having 3 to 20 C atoms, where in each case one or more non-adjacent $CH_2$ groups may be replaced by SO, SO$_2$, O, S and where one or more H atoms may be replaced by D, F, Cl, Br or I, or an aromatic or heteroaromatic ring system having 5 to 24 C atoms;

Ar is on each occurrence, identically or differently, and aromatic of heteroaromatic ring system having 5 to 60 aromatic ring atoms, which may in each case also be substituted by one or more radicals $R^4$;

n is on each occurrence equal to 1 and wherein the OLED comprising the compound of the formula (2A), is employed as an electron-acceptor material in a hole-injection layer.

2. A formulation comprising at least one compound according to claim 1 and at least one solvent.

3. The OLED according to claim 1, wherein the compound is employed as the electron-acceptor material in the hole-injection layer as pure material, or in combination with one or more further compounds, where a proportion of the compound according to claim 1 is then comprised between 50.0 and 99.9% by vol. if the compounds are applied from a gas phase and 50.0 and 99.9% by weight if the compounds are applied from solution.

4. The OLED according to claim 3, wherein the OLED further comprises at least one hole-transport layer and at least one emitting layer, where the hole-transport layer is located between the hole-injection layer and the emitting layer.

5. The OLED according to claim 3, wherein the hole-injection layer comprising the compound has a thickness layer of from 0.5 nm to 50 nm.

6. The OLED according to claim 1, wherein the compound is employed as a p-dopant in a hole-transporting layer selected from a hole-injection layer, a hole-transport layer and an electron-blocking layer.

7. The OLED according to claim 1, wherein the compound is of the formula:

* * * * *